(12) United States Patent
Lazzari et al.

(10) Patent No.: US 7,659,407 B2
(45) Date of Patent: Feb. 9, 2010

(54) PHARMACEUTICAL COMPOUNDS

(75) Inventors: Paolo Lazzari, Cagliari (IT); Stefania Ruiu, Cagliari (IT); Gerard Aime Pinna, Sassari (IT); Gabriele Murineddu, Sassari (IT)

(73) Assignee: Neuroscienze Pharmaness S.C.a.R.L., Cagliari (IT)

( * ) Notice: Subject to any disclaimer, the term of this patent is extended or adjusted under 35 U.S.C. 154(b) by 187 days.

(21) Appl. No.: 11/134,627

(22) Filed: May 23, 2005

(65) Prior Publication Data
US 2005/0261281 A1    Nov. 24, 2005

(30) Foreign Application Priority Data
May 24, 2004    (IT)    .......................... MI2004A1032

(51) Int. Cl.
*A61K 31/4155*    (2006.01)
*A61K 31/454*    (2006.01)
*C07D 409/04*    (2006.01)
*C07D 409/14*    (2006.01)

(52) U.S. Cl. .................... 548/365.7; 514/326; 514/406; 546/211; 548/364.1

(58) Field of Classification Search ................ 548/365.7
See application file for complete search history.

(56) References Cited

U.S. PATENT DOCUMENTS

| | | |
|---|---|---|
| 5,462,960 A | 10/1995 | Barth et al. |
| 5,466,823 A | 11/1995 | Talley et al. |
| 5,504,216 A | 4/1996 | Holohan et al. |
| 5,508,426 A | 4/1996 | Holohan et al. |
| 5,510,496 A | 4/1996 | Talley et al. |
| 5,516,907 A | 5/1996 | Talley et al. |
| 5,521,207 A | 5/1996 | Graneto |
| 5,547,975 A | 8/1996 | Talley et al. |
| 5,563,165 A | 10/1996 | Talley et al. |
| 5,753,688 A | 5/1998 | Talley et al. |
| 5,756,529 A | 5/1998 | Isakson et al. |
| 5,760,068 A | 6/1998 | Talley et al. |
| 5,925,768 A | 7/1999 | Barth et al. |
| 6,028,084 A | 2/2000 | Barth et al. |
| 6,100,259 A | 8/2000 | Xiang et al. |
| 6,156,781 A | 12/2000 | Talley et al. |
| 6,217,860 B1 | 4/2001 | Woo et al. |
| 6,344,474 B1 | 2/2002 | Maruani et al. |
| 6,413,960 B1 | 7/2002 | Talley et al. |
| 6,432,984 B1 | 8/2002 | Barth et al. |
| 6,476,060 B2 | 11/2002 | Lange et al. |
| 6,492,411 B1 | 12/2002 | Talley et al. |
| 6,509,367 B1 | 1/2003 | Martin et al. |
| 6,586,603 B1 | 7/2003 | Talley et al. |
| 6,716,991 B1 | 4/2004 | Talley et al. |
| 6,951,949 B2 | 10/2005 | Talley et al. |
| 7,157,470 B2 | 1/2007 | Smallheer et al. |
| 7,393,842 B2 | 7/2008 | Makriyannis et al. |
| 2001/0053788 A1 | 12/2001 | Lange et al. |
| 2003/0003145 A1 | 1/2003 | Abramovici et al. |
| 2004/0039024 A1 | 2/2004 | Barth et al. |
| 2004/0192667 A1 | 9/2004 | Makriyannis et al. |
| 2004/0192930 A1 | 9/2004 | Talley et al. |
| 2004/0204406 A1 | 10/2004 | Nazare et al. |
| 2005/0096379 A1 | 5/2005 | Martin et al. |
| 2005/0101592 A1 | 5/2005 | Carpino et al. |
| 2005/0131050 A1 | 6/2005 | Talley et al. |
| 2006/0030563 A1 | 2/2006 | Makriyannis et al. |
| 2006/0100208 A1 | 5/2006 | Makriyannis et al. |

FOREIGN PATENT DOCUMENTS

| | | |
|---|---|---|
| DE | 102 39 832 A1 | 3/2004 |
| EP | 0 477 049 A1 | 3/1992 |
| EP | 0 656 354 A1 | 6/1995 |
| EP | 0731795 B1 | 12/1999 |

(Continued)

OTHER PUBLICATIONS

Gorbunova et al., CA 80:70640, 1974.*

(Continued)

*Primary Examiner*—Laura L. Stockton
(74) *Attorney, Agent, or Firm*—Knobbe Martens Olson & Bear LLP

(57) ABSTRACT

Pyrazole derivatives of the following formula (I), having affinity for the cannabinoidergic CB1 and/or CB2 receptors:

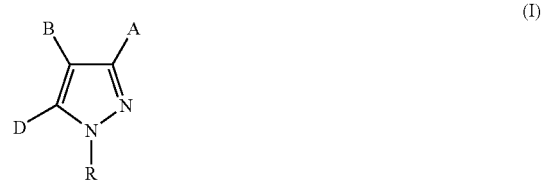

(I)

wherein:
R is a group selected from:
$C_1$-$C_{10}$ alkyl;
aryl, arylalkyl or arylalkenyl, not substituted or having from one to four substituents, equal to or different from each other;
A is a group selected from the following:
an ether group of formula —$(CH_2)$—O—$(CH_2)_v$—R" wherein
v is equal to 1 or 2;
R" is as defined in the present application;
a ketone group of formula —C(O)—Z', wherein Z' is as defined in the present application;
a substituent having an hydroxyl function of formula —CH(OH)—Z', Z' being as defined in the present application;
an amide substituent of formula —C(O)—NH—T', T' being as defined in the present application;
B is a group as defined in the present application;
D is an heteroaryl optionally substituted.

11 Claims, No Drawings

FOREIGN PATENT DOCUMENTS

| | | |
|---|---|---|
| EP | 1 216 980 A1 | 6/2002 |
| EP | 1 230 222 B1 | 8/2002 |
| EP | 1 230 244 B1 | 8/2002 |
| EP | 0854723 B1 | 4/2003 |
| EP | 1571147 A2 | 9/2005 |
| WO | WO 95/15316 | 6/1995 |
| WO | WO 97/11704 | 4/1997 |
| WO | WO 01/29007 A2 | 4/2001 |
| WO | WO 03/020217 A2 | 3/2003 |
| WO | WO 03/026652 A1 | 4/2003 |
| WO | WO 2004/016592 A1 | 2/2004 |
| WO | WO 2004/056815 A1 | 7/2004 |
| WO | WO 2005/016877 A2 | 2/2005 |
| WO | WO 2005/063737 A1 | 7/2005 |
| WO | WO 2006/076442 A2 | 7/2006 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*

Vippagunta et al. (Advanced Drug Delivery Reviews, 48 (2001), pp. 3-26.*

Q. Lu et al., "Expression of CB2 cannabinoid receptor mRNA in adult rat retina", *Visual Neurosciencecol* 17, 91-95, 2000.

M. Glass, "The Role of Cannabinoids in Neurodegenerative Diseases," *Prog. Neoro-Psychopharmacol. & Biol. Psychiatri.* 25, 743-765, 2001.

A. Porcella et al., "Cannabinoid receptor $CB_1$, mRNA is highly expressed in the rat ciliary body: implications for the antiglaucoma properties of marihuana[1]", *J. Pharmacol. Exp. Ther.* 58, 240-245, 1998.

A. Porcella et al., "The human eye expresses high levels of CB1 cannabinoid receptor mRNA and protein", *European Journal of Neorosci* 12, 1-5, 2000.

M. Pacheco et al., "Aminoalkylindoles: Actions on Specific G-Protein-Linked Receptors[1]", *J. Pharmacol. Exp. Ther.* 257, 170-182, 1991.

B.R. Martin et al., "Behavioral, Biochemical, and Molecular Modeling Evaluations of Cannabinoid Analogs", *Pharmacol. Biochem. Behav.* 40, 471-478, 1991.

P.B. Smith et al., "The Pharmacological Activity of Anandamine, a Putative Endogenous Cannabinold, in Mice", *J. Pharmacol. Exp. Ther.* 270, 219-227, 1994.

M. Rinaldi-Carmona et al., "SR 141716A, a potent and selective antagonist of the brain cannbinoid receptor", *FEBS Lett.*, 350, 240-244, 1994.

M. Rinaldi-Carmona at al., "SR 144528, the First Potent and Selective Antagonist of the CB2 Cannabinold Receptor", *J. Pharmacol. Exp. Ther.* 284, 644-650, 1998.

Remington: The Science and Practice of Pharmacy, II, 1457, 1995.

R.G. Pertwee, "Further evidence for the presence of cannabinoid $Cb_1$ receptors in guinea-pig small intestine", Br. J. Pharmacol. 118, 2199-2205—1996.

G. Colombo of al., "Cannabinoid modulation of intestinal propulsion in mice", *Eur. J. Pharmacol.* 344, 67-69, 1998.

M. A. Casu at al., "Differential distribution of functional cannabinoid $CB_1$ receptors in the mouse gasstroenteric tract", *Eur. J. Pharmacol.* 459, 97-105, 2003.

Y. Nagakura et al., "Compounds possessing $5-HT_3$ receptor antagonistic activity inhibit intestinal propulsion in mice". *Eur. J. Pharmacol.* 311, 67-72, 1996.

Katoch-Rouse of al., "Synthesis, Structure-Activity Relationship, and Evaluation of SR141716 Analogues: Development of Central Cannabinoid Receptor Ligands with Lower Lipophilicity", J. Med. Chem. 46, 642-645, 2003.

XP-002340680—Database Accession No. BRN: 837518 & Chem. Heterocycl. Compd., 9, 1374, 1973.

XP-002340681—Database Accession No. BRN: 828894 & Chem. Heterocycl. Compd., 9, 1374, 1973.

XP-002340682—Database Accession No. BRN: 181189 & Gazz. Chim. Ital., 88, 879-896, 1958.

XP-002340683—Database Accession No. BRN: 248827 & Gazz. Chim. Ital., 88, 879-896, 1958.

XP-002340684—Database Accession No. BRN: 6874802 & Farmaco Ed. Sci., 40(4), 259-271, 1985.

XP-002340685—Database Accession No. BRN: 303837 & Gazz. Chim. Ital., 89, 964-976, 1959.

Yanborisov et al., "Synthesis and Pharmacological Characterization of Heteroylpyruvic Acids and Their Derivatives", Phar. Chem. J., 32(9), 480-482, 1998.

* cited by examiner

PHARMACEUTICAL COMPOUNDS

The present invention relates to pyrazole derivatives having affinity for cannabinoidergic CB1 and/or CB2 receptors to the corresponding solvates and pharmaceutically acceptable salts and to their pharmaceutical compositions.

More specifically the present invention relates to pyrazole derivatives containing a hetrocyclic ring having affinity for cannabinoidergic CB1 and/or CB2 receptors.

Cannabinoids are compounds deriving from sativa Cannabis, commonly known as marijuana. Among the at least 66 cannabinoid compounds characterizing the marijuana, tetrahydrocannabinols (THC) and $\Delta^9$-tetrahydrocannabinol ($\Delta^9$-THC) in particular, are considered as the most active. The properties which have indeed led to the use of marijuana as therapeutic agent of natural origin in mammalians and in men have been connected to the above compounds. Said properties are the following: the analgesic effect, the antiinflammatory activity, the reduction of the blood and intraocular pressure, the antihemetic activity. The negative effects which are associated to the marijuana use have furthermore been correlated to tetrahydrocannabinols, with particular reference to the psychological distortion of the perception, to the motor coordination loss, to the euphory, to the sedative effect. The cannabinoid pharmacological action appears directly correlated to their affinity towards two different classes of specific receptors belonging to the "G protein-coupled" receptor family: CB1 receptors, located in the central nervous system besides in the peripheral tissues, and CB2 receptors, identified in the cerebellum (Q. J. Lu et al.; *Visual Neurosci.;* 2000, 17, 9, 1-95) but which mainly find in the peripheral tissues (M. Glass; *Progr. Neuro-Psychopharmacol. & Biol. Psychiat.;* 2001, 25, 743-765). In the brain, the CB1 receptors are largely expressed in the hipocampus, in the cortical regions, in the cerebellum and inside the basal ganglia. Among the peripheral tissues wherein the CB1 receptors have been located, we remember testicles, small intestine, bladder, deferent duct. The CB1 receptors have furthermore been identified in the rat eye and in the human eye, in the retina and in the iris and in the ciliary body (A. Porcella et al.; *Molecular Brain Research;* 1998, 58, 240-245; A. Porcella et al.; *European Journal of Neuroscience;* 2000, 12, 1123-1127). The CB2 receptors are instead mainly located in the marginal spleen zones, in tonsils, besides in several immune system cells, as macrophages, monocytes, cells of the bone marrow, of thymus and pancreas. Other immune system cells wherein the CB2 receptors are significantly present are the T4 and T8 cells, the polymorphonucleate leucocytes, in particular the cells called natural killers and lymphocytes B.

The compounds capable to interact, as agonists or antagonists, with the CB2 receptors can therefore be used in the treatment of diseases wherein immune system cells or immune disorders are involved. The activation (modulation) of the CB2 receptors is also important in the treatment of other diseases, as for example in the osteoporosis, renal ischemia treatment and in inflammatory states.

The compounds with affinity towards the CB1 receptors can be used in the treatment of eye-diseases as glaucoma, lung-diseases as asthma and chronic bronchitis, inflammations as for example arthritis, allergies and allergic reactions as for example allergic rhinitis, contact dermatitis, allergic conjunctivitis. Such compounds can also be used in the pain treatment, in anxiety cases, in mood problems, delirium states, psychotic afflictions in general, besides for schizophrenia, depression treatment and when abuse and/or dependency substances are used (for example alcoholism and tabagism). The same compounds can also be used to contrast vomit, nausea, giddiness, especially in case of patients submitted to chemotherapy; in the treatment of neuropathies, hemicrania, stress, diseases having a psychosomatic origin, epilepsy, Tourette syndrome, Parkinson disease, Huntington disease, Alzheimer disease, senile dementia, and in case of cognitive disease and memory loss.

Further applications of the compounds having affinity towards CB1 receptors are the treatment of pathologies related to the appetite (obesity, bulimia), pathologies of the gastrointestinal tract and of the bladder, cardiovascular diseases, urinary and fertility problems, neuroinflammatory pathologies as for example multiple sclerosis, Guillain-Barré syndrome, viral encephalitis. For example some CB1 agonist active principles are successfully used in the nausea and vomit treatment associated to the chemotherapy and in the appetite stimulation in AIDS' patients. Compounds with antagonist activity towards CB1 receptors can be used for example in the treatment of psychosis, anxiety, depression, schizophrenia, obesity, neurological diseases (for example dementia, Parkinson disease, Alzheimer disease, epilepsy, Tourette syndrome), in memory loss, in the pain treatment, in central nervous system disease involving the neurotransmission of cannabinoids, in the treatment of gastrointestinal and/or cardiovascular troubles.

In connection with the wide pharmacological cannabinoid applications, over the last years several studies have been started to find endocannabinoids and for the synthesis of new compounds capable to selectively interact towards the two subclasses of cannabinoidergic CB1 and CB2 receptors. The researches have led on the one hand to the identification of anandamide endocannabinoids (arachidonyl ethanolamide) and 2-arachidonyl glycerol, on the other hand to the obtainment of different classes of synthesis compounds, agonists or antagonists towards the CB1 or CB2 receptors.

The class of the compounds having agonist activity towards the CB1 receptors (cannabimimetic activity) comprises synthesis compounds having a base structure directly derived from that of $\Delta^9$-THC, as (−)-11-OH-$\Delta^8$THC-dimethylheptyl (HU210) and nabilone, and compounds structurally different from $\Delta^9$-THC, as aminoalkylindols of the WIN 55,212-2 series (M. Pacheco et al.; *J. Pharmacol. Exp. Ther.;* 1991, 257, 1701-183) or as bicyclic cannabinols (non classic cannabinoids) referring to the compound CP 55,940 (M. Glass; *Progr. Neuro-Psychopharmacol. & Biol. Psychiat.;* 2001, 25, 743-765). The compounds having cannabimimetic activity show in vivo the following effects: hypoactivity, hypothermia, analgesia and catalepsy (B. R. Martin et al.; *Pharmacol. Biochem. Behav.;* 1991, 40, 471-478; P. B. Smith et al.; *J. Pharmacol. Exp. Ther.;* 1994, 270, 219-227).

Another class of synthesis compounds which have shown themselves particularly similar and selective towards cannabinoidergic receptors is that of the 3-pyrazole carboxylic acid derivatives. The reference compound of this class of derivatives is commonly indicated with the abbreviation SR141716A: [N-piperidino-5-(4-chlorophenyl)-1-(2,4-dichlorophenyl)-4-methylpyrazol-3-carboxyamide], described in EP 656,354. In particular the SR141716A compound has shown the following properties: a high affinity for the CB1 receptors (Ki=1.98±0.36 nM), a significant selectivity towards the CB1 receptors (affinity towards the CB1 receptors about a thousand times higher than that for the CB2 receptors), capability of inhibiting the cannabinoid activity, therefore antagonist activity, in samples in vivo and in vitro (M. Rinaldi-Carmona et al.; *FEBS Lett.;* 1994, 350, 240-244). On the basis of the properties pointed out, besides of several clinical and preclinical studies, the SR141716A compound, lately renamed by Sanofi-Synthélabo Rimonabant®, is designed to be mainly used as antihunger active principle in the obesity treatment as well as in the tabagism treatment.

Patent application US 2001/0053788 describes 4,5-dihydro-1H-pyrazole compounds as potential antagonists of the CB1 receptors. The general formula of the claimed compounds is reported hereinafter:

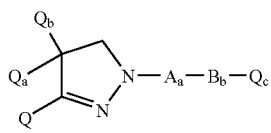

wherein: $Q$, $Q_a$, $Q_b$, $Q_c$, $A_a$, $B_b$ have different meanings.

Compounds having high affinity for the cannabinoidergic receptors and, especially, high selectivity for the CB1 receptors, are described in EP 1,230,244. In particular, said compounds are tricyclic analogues of SR141716A having general structure:

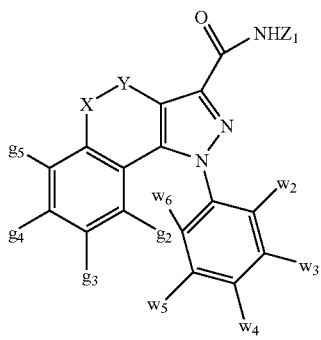

wherein $Z_1$, $w_2$, $w_3$, $w_4$, $w_5$, $w_6$, $g_2$, $g_3$, $g_4$, $g_5$ have different meanings; X—Y— represent a group selected from:

—(CH$_2$)$_r$—CH$_2$—, —CH$_2$—S(O)$_p$—, —S(O)$_p$—CH$_2$—, with r equal to 1 or 2, p equal to zero, 1 or 2. Compounds having high affinity for the cannabinoidergic receptors and, above all, high selectivity for CB2 receptors, are described in EP 1,230,222. In particular, the compounds described in this patent are tricyclic analogues of SR141716A having general structure:

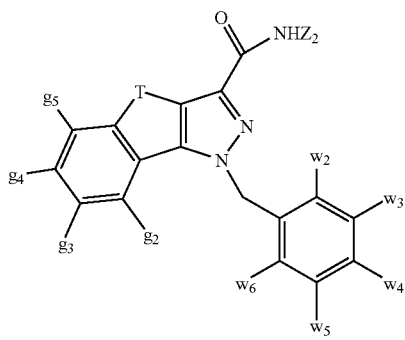

wherein: —T— represents a —(CH$_2$)$_m$— group, with m equal to 1 or 2; $Z_2$, $w_2$, $w_3$, $w_4$, $w_5$, $w_6$, $g_2$, $g_3$, $g_4$, $g_5$ have different meanlings.

Other compounds having a pyrazole structure capable to modulate the CB2 receptors are described in U.S. Pat. No. 6,100,259 and are represented by the general formula:

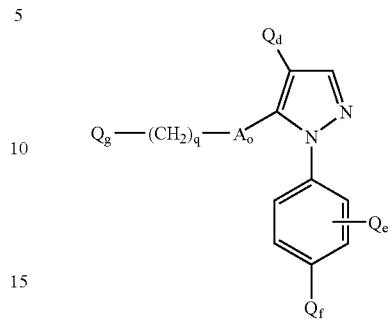

wherein q is between 1 and 6, while $A_o$, $Q_d$, $Q_e$, $Q_f$, $Q_g$ have different meanings.

A further compound having a pyrazole structure with affinity and selectivity towards CB2 receptors is the compound known with the abbreviation SR144528 (M. Rinaldi-Carmona et Al. J. Pharmacol. Expt. Ther. 1998 284 644-650) the structure of which is reported hereinafter:

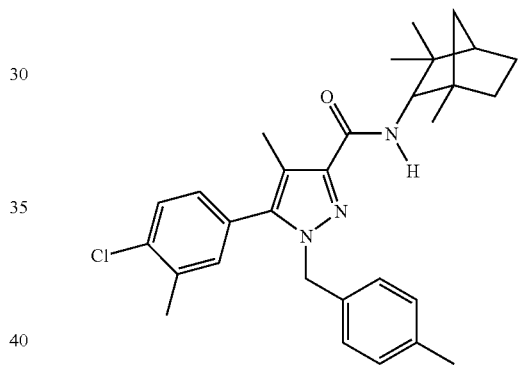

Another compound known for its selectivity towards the CB2 receptors, having agonist activity towards this subclass of receptors, is the compound 1-propyl-2-methyl-3-naphthoyl-indole, called JWH-015 (M. Glass; *Progr. Neuro-Psychopharmacol. & Biol. Psychiat.;* 2001, 25, 743-765).

There was still the need of other compounds having affinity for the cannabinoidergic CB1 and/or CB2 receptors.

An object of the present invention are pyrazole derivatives of formula (I), having affinity for the cannabinoidergic CB1 and/or CB2 receptors:

(I)

wherein:
R is a group selected from the following:
linear or branched $C_1$-$C_{10}$ alkyl, wherein the end of the main chain not linked to the nitrogen atom has —CH₂—W termination, W being a group selected from hydrogen, halogen, isothiocyanate, CN, OH, OCH₃, NH₂, —CH═CH₂;

aryl, arylalkyl or arylalkenyl, not substituted or having from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle, phenyl;

A is a group selected from the following:

an ether group of formula: —(CH₂)—O—(CH₂)ᵥ—R″, wherein:
  v is an integer equal to 1 or 2;
  R″ is a saturated or unsaturated heterocycle, or a $C_3$-$C_{15}$ cycloalkyl, or an aryl, or a heteroaryl;

a ketonic group of formula —C(O)—Z′, wherein Z′ is as defined below;

a substitutent having an hydroxyl function of formula —CH(OH)—Z′, Z′ being a $C_1$-$C_8$ alkyl or a $C_3$-$C_{15}$ cycloalkyl, a saturated or unsaturated heterocycle, or an aryl, or a heteroaryl;

an amidic substituent of formula —C(O)—NH—T′, T′ being a group selected from:
  $C_1$-$C_8$ alkyl;
  $C_1$-$C_7$ haloalkyl;
  aryl, arylalkyl or arylalkenyl, optionally containing one heteroatom selected among S, N, O, not substituted or optionally having from one to five substituents, said substituents equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy;
  a $C_3$-$C_{15}$ cycloalkyl not substituted or substituted with one or more $C_1$-$C_7$ alkyl chains, said chains being from one to four for $C_5$-$C_{15}$ cycloalkyls, being from one to three for the $C_4$ cycloalkyl, being from one to two for the $C_3$ cycloalkyl, said alkyl groups being equal to or different from each other;
  a group having formula:

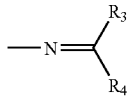

(IA)

wherein R₃ and R₄ equal to or different from each other, represent hydrogen or $C_1$-$C_3$ alkyl, with the proviso that R₃ and R₄ are not both hydrogen;

a group having formula:

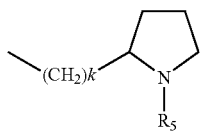

(IB)

wherein R₅ represents a $C_1$-$C_3$ alkyl and k is an integer between 1 and 3;

a group NR₁R₂, wherein R₁ and R₂, equal or different, have the following meanings:
  hydrogen;
  $C_1$-$C_7$ alkyl;

aryl, arylalkyl or arylalkenyl not substituted or optionally having on the aromatic rings from one to four substituents, equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy, wherein in the previous substituents comprising $C_1$-$C_7$ aliphatic chains, $C_1$-$C_3$ chains are preferably used;

or R₁ and R₂ together with the nitrogen atom to which they are linked form a, saturated or unsaturated, heterocycle from 5 to 10 carbon atoms, not substituted or optionally having from one to four substituents, equal to or different from each other, selected from $C_1$-$C_7$ alkyl, phenyl, benzyl, said phenyl or benzyl optionally substituted with one or more groups, equal to or different from each other, selected from: halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy.

B is a group selected from: halogen; hydrogen; $C_1$-$C_4$ alkyl; $C_1$-$C_6$ haloalkyl; $C_1$-$C_6$ haloalkoxy; $C_1$-$C_6$ alkylthio; $C_1$-$C_6$ alkoxy; $C_1$-$C_6$ hydroxyalkyl; $C_1$-$C_6$ hydroxyalkoxy; cyanomethyl; $C_1$-$C_6$ alkylsulphonyl; $C_1$-$C_6$ alkylsulphinyl; —CH₂—NR₆R₇; wherein:

R₆ and R₇, equal to or different, represent each separately:
  hydrogen;
  $C_1$-$C_7$ alkyl;
  aryl, arylalkyl or arylalkenyl as defined below, optionally containing a heteroatom selected from S, N, O, not substituted or optionally having from one to five substituents, said substituents equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy;

or R₆ and R₇ together with the nitrogen atom to which they are linked form a saturated or unsaturated heterocycle from 5 to 10 carbon atoms, not substituted or optionally having from one to four substituents, equal to or different from each other, selected from $C_1$-$C_7$ alkyl, phenyl, benzyl, said phenyl or benzyl optionally substituted with one to five groups, equal to or different from each other, selected from: halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy.

D is an heteroaryl as defined below, optionally substituted with a number of substituents ranging from 1 to 5 compatibly with the number of the ring atoms, said substituents equal to or different from each other, selected from: halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, isothiocyanate, phenyl, cycloalkyl, saturated or unsaturated heterocycle, heteroaryl.

Where not otherwise specified, in the whole text:
  the term "alkyl" means a $C_1$-$C_{20}$ saturated hydrocarbon chain linear or branched when possible;
  the term "alkenyl" means a $C_2$-$C_{20}$ mono- or polyunsaturated, preferably mono-unsaturated hydrocarbon chain linear or branched;
  the term "cycloalkyl" means an aliphatic monocyclic ring, for example from 3 to 8 carbon atoms, in particular from 4 to 6 carbon atoms, and a polycyclic structure from 8 to 19 carbon atoms; wherein the ring or the rings do not contain unsaturations;
  the term "saturated heterocycle" means a cycloalkyl as above wherein at least one carbon atom is substituted by one heteroatom selected from S, O, N; when the ring is monocyclic, preferably the heteroatoms are no more than 2;

the term "unsaturated heterocycle" means a cycloalkyl as above having one or more double bonds, with the proviso that the structure does not result of aromatic type, wherein at least one carbon atom is substituted by one heteroatom selected from S, O, N;

the term "halogen" indifferently indicates an atom selected from fluorine, chlorine, bromine, iodine;

the term "haloalkyl" means an alkyl according to the above definition, wherein one or more hydrogen atoms are substituted by as many halogen atoms; for example trifluoromethyl, 1-bromo-n-butyl, pentachloroethyl;

the term "aryl" means a $C_6$ monocyclic aromatic radical, or a $C_8$-$C_{19}$ polycyclic radical wherein at least one ring is aromatic, exclusively containing carbon atoms and hydrogen atoms;

the term "heteroaryl" means an aryl as above, except that the monocyclic radical is $C_5$-$C_6$ wherein at least one carbon atom is substituted by one heteroatom selected from S, O, N; preferably the heteroatoms in case of monocyclic radicals are no more than 2;

the term "arylalkyl" means an alkyl as above, preferably $C_1$-$C_7$, linked to an aryl as above, for example benzyl;

the term "arylalkenyl" means an alkenyl as above linked to an aryl as above;

with "compound having affinity towards the receptors" it is meant a compound which has in vivo agonist, or antagonist, or partial agonist, or partial antagonist, or opposite agonist, or opposite antagonist, or opposite partial agonist activity towards receptors. The meaning of such terms is well known to the skilled man in the field.

The preferred compounds of formula (I) are those wherein:

R is a group selected from the following:
a linear or branched $C_1$-$C_5$ alkyl, wherein the end of the main chain not linked to the nitrogen atom has —$CH_2$—W termination, W being a halogen group;
aryl, arylalkyl or arylalkenyl not substituted or containing from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle, phenyl;

A is an amide substituent group of formula:
—C(O)—NH—T', wherein T' has the meanings reported for formula (I), excluding the formulas (IA) and (IB);

B is a group selected from: $C_1$-$C_4$ alkyl; $C_1$-$C_6$ haloalkyl; $C_1$-$C_6$ haloalkoxy; $C_1$-$C_6$ alkylthio; $C_1$-$C_6$ alkoxy; $C_1$-$C_6$ hydroxyalkyl; $C_1$-$C_6$ hydroxyalkoxy; cyanomethyl; —$CH_2$—$NR_6R_7$; wherein: $R_6$ and $R_7$, equal to or different, have the meanings indicated above in formula (I) excluding hydrogen;

D is a heteroaryl with ring from 5 to 6 atoms, optionally substituted with a number of substituents ranging from 1 to 4 for the ring having 5 atoms and from 1 to 5 for the ring having 6 atoms, said substituents equal to or different from each other, selected from the following: halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, isothiocyanate, phenyl, cycloalkyl, saturated or unsaturated heterocycle, heteroaryl.

The compounds of formula (I) are still more preferred, wherein:

R is a group selected from the following:
linear or branched $C_1$-$C_5$ alkyl, wherein the end of the main chain not linked to the nitrogen atom has —$CH_2$—W termination, W being a halogen group;
aryl, arylalkyl or arylalkenyl, not substituted or having from one to five substituents, equal to or different from each other, selected from halogen, $C_1$-$C_3$ alkyl, $C_1$-$C_3$ alkylthio, $C_1$-$C_3$ alkoxy, $C_1$-$C_3$ haloalkyl, $C_1$-$C_3$ haloalkoxy;

A is an amide substituent group of formula:
—C(O)—NH—T', wherein T' has the following meanings:
$C_1$-$C_8$ alkyl;
$C_1$-$C_7$ haloalkyl;
aryl, arylalkyl or arylalkenyl, optionally containing one heteroatom, selected from N, S, O, not substituted or having from one to five substituents, equal to or different from each other, said substituents selected from halogen, $C_1$-$C_3$ alkyl, $C_1$-$C_3$ haloalkyl, $C_1$-$C_3$ haloalkoxy, $C_1$-$C_3$ alkylthio, $C_1$-$C_3$ alkoxy;
one group $NR_1R_2$, wherein $R_1$ and $R_2$ have the above values in formula (I);
a $C_3$-$C_{15}$ cycloalkyl not substituted or substituted with one or more $C_1$-$C_7$ alkyl chains, said chains being from one to four for $C_5$-$C_{15}$ cycloalkyls, being from one to three for the $C_4$ cycloalkyl, being from one to two for the $C_3$ cycloalkyl, said alkyl groups being equal to or different from each other;

B is a group selected from: $C_1$-$C_3$ alkyl; $C_1$-$C_3$ haloalkyl; $C_1$-$C_3$ haloalkoxy; $C_1$-$C_3$ alkylthio; $C_1$-$C_3$ alkoxy; $C_1$-$C_3$ hydroxyalkyl; $C_1$-$C_3$ hydroxyalkoxy; —$CH_2$—$NR_6R_7$; wherein: $R_6$ and $R_7$, equal or different, have the meanings indicated above in formula (I) excluding hydrogen;

D is an heteroaryl selected from the following: thiophene, pyridine, furan, oxazole, thiazole, imidazole, pyrazole, isoxazole, isothiazole, triazole, pyridazine, pyrimidine, pyrazine, triazine, pyrrole; said heteroaryls optionally substituted with one, two, three or four substituents, equal to or different from each other, selected from the following: halogen, $C_1$-$C_3$ alkyl, $C_1$-$C_3$ alkylthio, $C_1$-$C_3$ alkoxy, $C_1$-$C_3$ haloalkyl, $C_1$-$C_3$ haloalkoxy; preferably the heteroaryls having 5 atoms are used, still more preferably selected between thiophene and furan.

The compounds of formula (I) are preferably used, wherein A=—C(O)—NH-T' wherein T' is as above.

Examples of said compounds are the following:

N-piperidinyl-5-(5-chloro-thiophen-2-yl)-1-(2',4'-dichlorophenyl)-4-methyl-1H-pyrazol-3-carboxamide;

N-homopiperidinyl-5-(5-chloro-thiophen-2-yl)-1-(2',4'-dichlorophenyl)-4-methyl-1H-pyrazol-3-carboxamide;

N-pyrrolidinyl-5-(5-chloro-thiophen-2-yl)-1-(2',4'-dichlorophenyl)-4-methyl-1H-pyrazol-3-carboxamide;

p-Methoxyphenyl-5-(5-chloro-thiophen-2-yl)-1-(2',4'-dichlorophenyl)-4-methyl-1H-pyrazol-3-carboxamide;

p-Methoxyphenyl-5-(5-chloro-thiophen-2-yl)-1-(2',4'-dichlorophenyl)-4-methyl-1H-pyrazol-3-carbohydrazide;

N-piperidinyl-5-(5-bromo-thiophen-2-yl)-1-(2',4'-dichlorophenyl)-4-methyl-1H-pyrazol-3-carboxamide;

N-homopiperidinyl-5-(5-bromo-thiophen-2-yl)-1-(2',4'-dichlorophenyl)-4-methyl-1H-pyrazol-3-carboxamide;

N-pyrrolidinyl-5-(5-bromo-thiophen-2-yl)-1-(2',4'-dichlorophenyl)-4-methyl-1H-pyrazol-3-carboxamide;

p-Methoxyphenyl-5-(5-bromo-thiophen-2-yl)-1-(2',4'-dichlorophenyl)-4-methyl-1H-pyrazol-3-carboxamide;

p-Methoxyphenyl-5-(5-bromo-thiophen-2-yl)-1-(2',4'-dichlorophenyl)-4-methyl-1H-pyrazol-3-carbohydrazide;
N-piperidinyl-5-(5-methyl-thiophen-2-yl)-1-(2',4'-dichlorophenyl)-4-methyl-1H-pyrazol-3-carboxamide;
N-homopiperidinyl-5-(5-methyl-thiophen-2-yl)-1-(2',4'-dichlorophenyl)-4-methyl-1H-pyrazol-3-carboxamide;
N-pyrrolidinyl-5-(5-methyl-thophen-2-yl)-1-(2',4'-dichlorophenyl)-4-methyl-1H-pyrazol-3-carboxamide;
p-Methoxyphenyl-5-(5-methyl-thiophen-2-yl)-1-(2',4'-dichlorophenyl)-4-methyl-1H-pyrazol-3-carboxamide;
p-Methoxyphenyl-5-(5-methyl-thiophen-2-yl)-1-(2',4'-dichlorophenyl)-4-methyl-1H-pyrazol-3-carbohydrazide;
N-piperidinyl-5-(5-chloro-thiophen-2-yl)-1-(2',4'-dichlorophenyl)-4-ethyl-1H-pyrazol-3-carboxamide;
N-homopiperidinyl-5-(5-chloro-thiophen-2-yl)-1-(2',4'-dichlorophenyl)-4-ethyl-1H-pyrazol-3-carboxamide;
N-pyrrolidinyl-5-(5-chloro-thiophen-2-yl)-1-(2',4'-dichlorophenyl)-4-ethyl-1H-pyrazol-3-carboxamide;
p-Methoxyphenyl-5-(5-chloro-thiophen-2-yl)-1-(2',4'-dichlorophenyl)-4-ethyl-1H-pyrazol-3-carboxamide;
p-Methoxyphenyl-5-(5-chloro-thiophen-2-yl)-1-(2',4'-dichlorophenyl)-4-ethyl-1H-pyrazol-3-carbohydrazide;
N-piperidinyl-5-(5-bromo-thiophen-2-yl)-1-(2',4'-dichlorophenyl)-4-ethyl-1H-pyrazol-3-carboxamide;
N-homopiperidinyl-5-(5-bromo-thiophen-2-yl)-1-(2',4'-dichlorophenyl)-4-ethyl-1H-pyrazol-3-carboxamide;
N-pyrrolidinyl-5-(5-bromo-thiophen-2-yl)-1-(2',4'-dichlorophenyl)-4-ethyl-1H-pyrazol-3-carboxamide;
p-Methoxyphenyl-5-(5-bromo-thiophen-2-yl)-1-(2',4'-dichlorophenyl)-4-ethyl-1H-pyrazol-3-carboxamide;
p-Methoxyphenyl-5-(5-bromo-thiophen-2-yl)-1-(2',4'-dichlorophenyl)-4-ethyl-1H-pyrazol-3-carbohydrazide;
N-piperidinyl-5-(5-methyl-thiophen-2-yl)-1-(2',4'-dichlorophenyl)-4-ethyl-1H-pyrazol-3-carboxamide;
N-homopiperidinyl-5-(5-methyl-thiophen-2-yl)-1-(2',4'-dichlorophenyl)-4-ethyl-1H-pyrazol-3-carboxamide;
N-pyrrolidinyl-5-(5-methyl-thiophen-2-yl)-1-(2',4'-dichlorophenyl)-4-ethyl-1H-pyrazol-3-carboxamide;
p-Methoxyphenyl-5-(5-methyl-thiophen-2-yl)-1-(2',4'-dichlorophenyl)-4-ethyl-1H-pyrazol-3-carboxamide;
p-Methoxyphenyl-5-(5-methyl-thiophen-2-yl)-1-(2',4'-dichlorophenyl)-4-ethyl-1H-pyrazol-3-carbohydrazide.

The compounds of formula (I) of the present invention depending on the substituents can contain one or more chiral centres in their structure.

All the various isomers and the corresponding mixtures are considered included in the present invention. In the compounds of formula (I) cis-trans type isomers can also be present.

The Applicant has surprisingly and unexpectedly found that the compounds of formula (I) have affinity for the cannabinoidergic CB1 and/or CB2 receptors.

The above defined hydrates, solvates and pharmaceutically acceptable salts of the compounds of formula (I), comprising all the various isomers and the corresponding mixtures, are a further object of the present invention. The meaning of the terms "hydrate" and "solvate" is well known to the skilled man in the field.

A further object of the present invention is a process for preparing the compounds of general formula (I) comprising:
i. synthesis of the acid of the following general formula (II), or of one of its reactive derivatives, selected from acyl halides, anhydrides, mixed anhydrides, imidazolides, ester-amide adducts, linear or branched when possible $C_1$-$C_4$ alkyl esters:

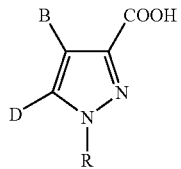

comprising the following steps:
obtainment of α-hydroxy-γ-ketoesters of formula (IV), wherein B and D are as previously defined, starting from a compound of formula (III) by reaction with an alkaline metal hydride, for example sodium hydride and diethyloxalate in a solvent inert under the reaction conditions, for example DMF, working at room temperature, or anyway between 15° C. and 30° C. (Claisen condensation):

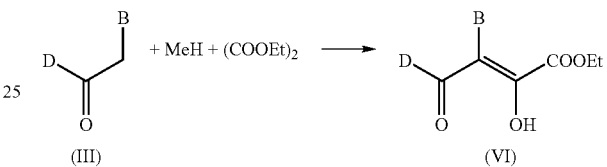

wherein Me is an alkaline metal;
reaction of the compounds of formula (IV) with a hydrazine of formula (V) wherein R is as previously defined, said compound (V) optionally being in the form of a hydrochloride salt, in alcoholic solvent or in acetic acid under reflux, to obtain the compound of formula (VI), ethyl ester of the acid of formula (II):

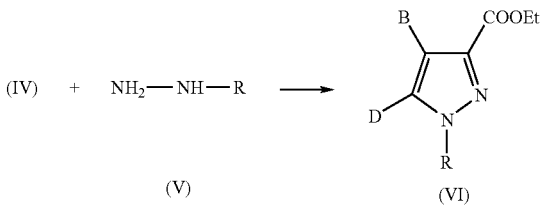

basic hydrolysis with alkaline hydroxides in hydroalcoholic solution of the compound of formula (VI) under reflux to obtain the acid of general formula (II);
optionally, formation of a reactive derivative of the acid of general formula (II), said derivative being as defined above;
ii) when in the general formula (I) A=—($CH_2$)—O—($CH_2$)$_v$—R'', wherein R'' is as above, the corresponding compounds can be prepared starting from the acid of formula (II) or from one of its esters, for example the ethyl ester, which is reduced in a first step, by operating at room temperature, into a primary alcohol in an inert solvent (for example tetrahydrofuran), for example by using an organic metal hydride, as di-isobutyl aluminum hydride, or lithium and aluminum hydride; then the obtained primary alcohol is reacted at room temperature with an alkyl halide of formula R''—($CH_2$)Hal, wherein Hal=halogen, in the presence of an alkaline hydride, for example sodium hydride, to obtain the above mentioned compounds, wherein A=—($CH_2$)—O—($CH_2$)$_v$—R''.

When in formula (I) A=—C(O)—Z', Z' being as above, the compounds of formula (I) can be prepared according to one of the following methods:

- by reacting an ester of the acid of general formula (II), preferably the ethyl ester with trialkylaluminum, preferably Al(CH$_3$)$_3$ with a hydrochloride salt of an amine, the amine being a hydrochloride salt preferably HN(OCH$_3$)CH$_3$.HCl in a solvent inert under the reaction conditions, preferably dichloromethane, initially at 0° C., then at room temperature until the ester disappearance; then by adding at 0° C. to the reaction mixture Z'MgBr, wherein Z' is as above, and allowing to react at room temperature until obtaining the compound of formula (I) wherein R'=—C(O)—Z';
- by reacting the acid of formula (II), or one of its reactive derivatives, with an organic metal salt of formula Z'$^-$ Me$^+$ wherein Me$^+$ is preferably an alkaline metal cation for example lithium, in a solvent inert under the reaction conditions, obtaining the compound of formula (I) wherein R'=—C(O)—Z'.

The former of the two above processes is preferably used.

When in the general formula (I) A=—CH(OH)—Z', wherein Z' is as above, the synthesis is carried out in two steps:

- preparation of the compound of formula (I) wherein R'=—C(O)—Z' by using one of the two reactions reported above;
- reaction of the compound of formula (I) wherein R'=—C(O)—Z' with lithium and aluminum hydride or sodium borohydride at room temperature to give the final product of formula (I) wherein A=—CH(OH)—Z'.

When in the general formula (I) A=—C(O)—NH—T', wherein T' is as above, the compounds are prepared by reaction in a solvent inert under the reaction conditions of the acid of formula (II) in the form of a corresponding reactive derivative as above, generally at room temperature with a compound of general formula:

H$_2$N—T'   (VII)

wherein T' has the previously defined meanings.

The compounds of formula (III) and (VII) are available on the market or are described in the publications of the field.

Preferred examples of acids of formula (II) are the following:

5-(5-Chloro-thiophen-2-yl)-1-(2',4'-dichloro-phenyl)-4-methyl-1H-pyrazol-3-carboxylic acid;
5-(5-Chloro-thiophen-2-yl)-1-(4-chloro-phenyl)-4-methyl-1H-pyrazol-3-carboxylic acid;
5-(5-Chloro-thiophen-2-yl)-1-(4-methoxy-phenyl)-4-methyl-1H-pyrazol-3-carboxylic acid;
5-(5-Bromo-thiophen-2-yl)-1-(2,4-dichloro-phenyl)-4-methyl-1H-pyrazol-3-carboxylic acid;
5-(5-Bromo-thiophen-2-yl)-1-(4-chloro-phenyl)-4-methyl-1H-pyrazol-3-carboxylic acid;
5-(5-Bromo-thiophen-2-yl)-1-(4-methoxy-phenyl)-4-methyl-1H-pyrazol-3-carboxylic acid;
5-(5-Methyl-thiophen-2-yl)-1-(2,4-dichloro-phenyl)-4-methyl-1H-pyrazol-3-carboxylic acid;
5-(5-Methyl-thiophen-2-yl)-1-(4-chloro-phenyl)-4-methyl-1H-pyrazol-3-carboxylic acid;
5-(5-Methyl-thiophen-2-yl)-1-(4-methoxy-phenyl)-4-methyl-1H-pyrazol-3-carboxylic acid;
5-(4-Chloro-thiophen-2-yl)-1-(2,4-dichloro-phenyl)-4-methyl-1H-pyrazol-3-carboxylic acid;
5-(4-Chloro-thiophen-2-yl)-1-(4-chloro-phenyl)-4-methyl-1H-pyrazol-3-carboxylic acid;
5-(4-Chloro-thiophen-2-yl)-1-(4-methoxy-phenyl)-4-methyl-1H-pyrazol-3-carboxylic acid;
5-(4-Bromo-thiophen-2-yl)-1-(2,4-dichloro-phenyl)-4-methyl-1H-pyrazol-3-carboxylic acid;
5-(4-Bromo-thiophen-2-yl)-1-(4-chloro-phenyl)-4-methyl-1H-pyrazol-3-carboxylic acid;
5-(4-Bromo-thiophen-2-yl)-1-(4-methoxy-phenyl)-4-methyl-1H-pyrazol-3-carboxylic acid;
5-(4-Methyl-thiophen-2-yl)-1-(2,4-dichloro-phenyl)-4-methyl-1H-pyrazol-3-carboxylic acid;
5-(4-Methyl-thiophen-2-yl)-1-(4-chloro-phenyl)-4-methyl-1H-pyrazol-3-carboxylic acid;
5-(4-Methyl-thiophen-2-yl)-1-(4-methoxy-phenyl)-4-methyl-1H-pyrazol-3-carboxylic acid;
5-(5-Chloro-furan-2-yl)-1-(2,4-dichloro-phenyl)-4-methyl-1H-pyrazol-3-carboxylic acid;
5-(5-Chloro-furan-2-yl)-1-(4-chloro-phenyl)-4-methyl-1H-pyrazol-3-carboxylic acid;
5-(5-Chloro-furan-2-yl)-1-(4-methoxy-phenyl)-4-methyl-1H-pyrazol-3-carboxylic acid;
5-(5-Bromo-furan-2-yl)-1-(2,4-dichloro-phenyl)-4-methyl-1H-pyrazol-3-carboxylic acid;
5-(5-Bromo-furan-2-yl)-1-(4-chloro-phenyl)-4-methyl-1H-pyrazol-3-carboxylic acid;
5-(5-Bromo-furan-2-yl)-1-(4-methoxy-phenyl)-4-methyl-1H-pyrazol-3-carboxylic acid;
5-(5-Methyl-furan-2-yl)-1-(2,4-dichloro-phenyl)-4-methyl-1H-pyrazol-3-carboxylic acid;
5-(5-Methyl-furan-2-yl)-1-(4-chloro-phenyl)-4-methyl-1H-pyrazol-3-carboxylic acid;
5-(5-Methyl-furan-2-yl)-1-(4-methoxy-phenyl)-4-methyl-1H-pyrazol-3-carboxylic acid;
5-(4-Chloro-furan-2-yl)-1-(2,4-dichloro-phenyl)-4-methyl-1H-pyrazol-3-carboxylic acid;
5-(4-Chloro-furan-2-yl)-1-(4-chloro-phenyl)-4-methyl-1H-pyrazol-3-carboxylic acid;
5-(4-Chloro-furan-2-yl)-1-(4-methoxy-phenyl)-4-methyl-1H-pyrazol-3-carboxylic acid;
5-(4-Bromo-furan-2-yl)-1-(2,4-dichloro-phenyl)-4-methyl-1H-pyrazol-3-carboxylic acid;
5-(4-Bromo-furan-2-yl)-1-(4-chloro-phenyl)-4-methyl-1H-pyrazol-3-carboxylic acid;
5-(4-Bromo-furan-2-yl)-1-(4-methoxy-phenyl)-4-methyl-1H-pyrazol-3-carboxylic acid;
5-(4-Methyl-furan-2-yl)-1-(2,4-dichloro-phenyl)-4-methyl-1H-pyrazol-3-carboxylic acid;
5-(4-Methyl-furan-2-yl)-1-(4-chloro-phenyl)-4-methyl-1H-pyrazol-3-carboxylic acid;
5-(4-Methyl-furan-2-yl)-1-(4-methoxy-phenyl)-4-methyl-1H-pyrazol-3-carboxylic acid;
5-(5-Chloro-thiophen-2-yl)-1-(2',4'-dichloro-phenyl)-4-ethyl-1H-pyrazol-3-carboxylic acid;
5-(5-Chloro-thiophen-2-yl)-1-(4-chloro-phenyl)-4-ethyl-1H-pyrazol-3-carboxylic acid;
5-(5-Chloro-thiophen-2-yl)-1-(4-methoxy-phenyl)-4-ethyl-1H-pyrazol-3-carboxylic acid;
5-(5-Bromo-thiophen-2-yl)-1-(2,4-dichloro-phenyl)-4-ethyl-1H-pyrazol-3-carboxylic acid;
5-(5-Bromo-thiophen-2-yl)-1-(4-chloro-phenyl)-4-ethyl-1H-pyrazol-3-carboxylic acid;
5-(5-Bromo-thiophen-2-yl)-1-(4-methoxy-phenyl)-4-ethyl-1H-pyrazol-3-carboxylic acid;
5-(5-Methyl-thiophen-2-yl)-1-(2,4-dichloro-phenyl)-4-ethyl-1H-pyrazol-3-carboxylic acid;
5-(5-Methyl-thiophen-2-yl)-1-(4-chloro-phenyl)-4-ethyl-1H-pyrazol-3-carboxylic acid;

5-(5-Methyl-thiophen-2-yl)-1-(4-methoxy-phenyl)-4-ethyl-1H-pyrazol-3-carboxylic acid;
5-(4-Chloro-thiophen-2-yl)-1-(2,4-dichloro-phenyl)-4-ethyl-1H-pyrazol-3-carboxylic acid;
5-(4-Chloro-thiophen-2-yl)-1-(4-chloro-phenyl)-4-ethyl-1H-pyrazol-3-carboxylic acid;
5-(4-Chloro-thiophen-2-yl)-1-(4-methoxy-phenyl)-4-ethyl-1H-pyrazol-3-carboxylic acid;
5-(4-Bromo-thiophen-2-yl)-1-(2,4-dichloro-phenyl)-4-ethyl-1H-pyrazol-3-carboxylic acid;
5-(4-Bromo-thiophen-2-yl)-1-(4-chloro-phenyl)-4-ethyl-1H-pyrazol-3-carboxylic acid;
5-(4-Bromo-thiophen-2-yl)-1-(4-methoxy-phenyl)-4-ethyl-1H-pyrazol-3-carboxylic acid;
5-(4-Methyl-thiophen-2-yl)-1-(2,4-dichloro-phenyl)-4-ethyl-1H-pyrazol-3-carboxylic acid;
5-(4-Methyl-thiophen-2-yl)-1-(4-chloro-phenyl)-4-ethyl-1H-pyrazol-3-carboxylic acid;
5-(4-Methyl-thiophen-2-yl) 1-(4-methoxy-phenyl)-4-ethyl-1H-pyrazol-3-carboxylic acid;
5-(5-Chloro-furan-2-yl)-1-(2,4-dichloro-phenyl)-4-ethyl-1H-pyrazol-3-carboxylic acid;
5-(5-Chloro-furan-2-yl)-1-(4-chloro-phenyl)-4-ethyl-1H-pyrazol-3-carboxylic acid;
5-(5-Chloro-furan-2-yl)-1-(4-methoxy-phenyl)-4-ethyl-1H-pyrazol-3-carboxylic acid;
5-(5-Bromo-furan-2-yl)-1-(2,4-dichloro-phenyl)-4-ethyl-1H-pyrazol-3-carboxylic acid;
5-(5-Bromo-furan-2-yl)-1-(4-chloro-phenyl)-4-ethyl-1H-pyrazol-3-carboxylic acid;
5-(5-Bromo-furan-2-yl)-1-(4-methoxy-phenyl)-4-ethyl-1H-pyrazol-3-carboxylic acid;
5-(5-Metil-furan-2-yl)-1-(2,4-dichloro-phenyl)-4-ethyl-1H-pyrazol-3-carboxylic acid;
5-(5-Methyl-furan-2-yl)-1-(4-chloro-phenyl)-4-ethyl-1H-pyrazol-3-carboxylic acid;
5-(5-Methyl-furan-2-yl)-1-(4-methoxy-phenyl)-4-ethyl-1H-pyrazol-3-carboxylic acid;
5-(4-Chloro-furan-2-yl)-1-(2,4-dichloro-phenyl)-4-ethyl-1H-pyrazol-3-carboxylic acid;
5-(4-Chloro-furan-2-yl)-1-(4-chloro-phenyl)-4-ethyl-1H-pyrazol-3-carboxylic acid;
5-(4-Chloro-furan-2-yl)-1-(4-methoxy-phenyl)-4-ethyl-1H-pyrazol-3-carboxylic acid;
5-(4-Bromo-furan-2-yl)-1-(2,4-dichloro-phenyl)-4-ethyl-1H-pyrazol-3-carboxylic acid;
5-(4-Bromo-furan-2-yl)-1-(4-chloro-phenyl)-4-ethyl-1H-pyrazol-3-carboxylic acid;
5-(4-Bromo-furan-2-yl)-1-(4-methoxy-phenyl)-4-ethyl-1H-pyrazol-3-carboxylic acid;
5-(4-Methyl-furan-2-yl)-1-(2,4-dichloro-phenyl)-4-ethyl-1H-pyrazol-3-carboxylic acid;
5-(4-Methyl-furan-2-yl)-1-(4-chloro-phenyl)-4-ethyl-1H-pyrazol-3-carboxylic acid;
5-(4-Methyl-furan-2-yl)-1-(4-methoxy-phenyl)-4-ethyl-1H-pyrazol-3-carboxylic acid.

With pharmaceutically acceptable salts all the salts are meant obtained by treating the compounds of formula (I) with organic or inorganic acids acceptable from the pharmaceutical point of view. For example hydrochlorides, sulphates, fumarates, oxalates, citrates, hydrogensulphates, succinates, paratoluensulphonates can be mentioned. See the publication: "Remington, The Science and Practice of Pharmacy", Vol. II, 1995, page 1457.

A further object of the present invention is represented by the pharmaceutical compositions containing the compounds of general formula (I), comprising the isomers and their mixtures, the corresponding hydrates or solvates or pharmaceutically acceptable salts.

With pharmaceutical compositions, preparations are meant wherein the active principles of formula (I), comprising all the different isomers and the corresponding mixtures, or the corresponding hydrates or solvates or pharmaceutically acceptable salts, are mixed with excipients, carriers, dyes, preservatives, flavorings and other additives the use of which is known in the pharmaceutical field.

The pharmaceutical compositions of the present invention can be administered by os, subcutaneous, sublingual, intramuscular, intravenous, topical, transdermal, rectal, ophtalmic, intranasal route. Said pharmaceutical compositions comprise for example dispersions, solutions, emulsions, microemulsions, powders, capsules, aerosol, suppositories, tablets, syrups, elixir, creams, gels, ointments, plasters.

The pharmaceutical compositions of the present invention can be obtained according to known methods of the pharmaceutical technique. For example, said pharmaceutical compositions can be obtained according to the processes indicated in U.S. Pat. No. 6,028,084, herein incorporated by reference.

The pharmaceutical compositions can also be prepared by using the methods and the additives indicated in patent application US2003/0003145. In these formulations sodium alkylsulphate or another surfactant commonly utilized in the pharmaceutical field can be used.

For example pharmaceutical compositions, usable for the oral administration of the compounds of formula (I) or of the corresponding hydrates or solvates or pharmaceutically acceptable salts, are formed of: 0.5-20% by weight of a compound of formula (I), comprising all the various isomers and the corresponding mixtures or of a corresponding hydrate or solvate or pharmaceutically acceptable salt; 0.05-0.5% by weight of sodium alkylsulphate or another surfactant; 2.5-10% by weight of a disgregating agent as for example cellulose, sodium carboxymethylcellulose or other cellulose derivatives.

The compounds of formula (I), including the various isomers and related mixtures, and the corresponding hydrates or solvates and pharmaceutically acceptable salts and their pharmaceutical compositions of the present invention have a high affinity in vitro for the cannabinoidergic CB1 and/or CB2 receptors. See the Examples. More specifically the compounds of the present invention have a Ki value for the CB1 and/or CB2 receptors lower than 0.5 µM.

The present invention also relates to the use of compounds of formula (I), including the various isomers and the respective mixtures, the corresponding hydrates or solvates or pharmaceutically acceptable salts, or the pharmaceutical compositions containing them, for preparing products for the treatment in mammalians and in men of diseases wherein the CB1 and/or CB2 receptors are involved.

In particular the compounds of formula (I) comprising the various isomers and respective mixtures, or the corresponding hydrates or solvates or pharmaceutically acceptable salts, or in the form of the corresponding pharmaceutical compositions, having affinity towards the CB2 receptors, can therefore be used in the treatment of diseases in which immune system cells or immune disorders are involved, or in the treatment of other pathologies, as for example osteoporosis, renal ischemia and in case of inflammatory states.

The compounds of the present invention, including the various isomers and respective mixtures, and the corresponding hydrates or solvates and pharmaceutically acceptable salts and the respective pharmaceutical compositions, having affinity towards the CB2 receptors, can also be used in case of diseases related to organ transplants and preventive rejection therapies in the allogenic transplant, in the transplant rejection treatment also in patients which have received other immunosuppressive therapies, in the treatment and prophylaxis of GVHD (Graft Versus Host Disease), in the treatment of diseases as: erythematous systemic lupus, ankylosing spondylitis, polyarthritis rheumatoid, hemolytic autoimmune anaemia, Behcet disease, Sjögren syndrome, undifferentiated spondylarthritis, reactive arthritis, dermatomyositis.

Furthermore the compounds of formula (I) comprising the various isomers and respective mixtures or the corresponding hydrates or solvates or pharmaceutically acceptable salts, or in the form of the corresponding pharmaceutical compositions, having affinity towards the CB1 receptors, can be used in the treatment of ocular diseases, as glaucoma or ocular hypertonia, lung-diseases as asthma and chronic bronchitis, allergies and allergic reactions (for example allergic rhinitis, contact dermatitis, allergic conjunctivitis), inflammations as for example arthritis.

The compounds of formula (I) comprising the various isomers and respective mixtures and the corresponding hydrates or solvates and pharmaceutically acceptable salts and the respective pharmaceutical compositions, having affinity towards the CB1 receptors, can also be used as analgesics in the pain treatment, in cases of anxiety, of mood problems, delirium states, psychotic afflictions in general, for the schizophrenia, depression treatment, when abuse and/or addiction substances are used (for example alcoholism and tabagism).

The compounds of formula (I) comprising the various isomers and respective mixtures and the corresponding hydrates or solvates and pharmaceutically acceptable salts and the respective pharmaceutical compositions, having affinity towards the CB1 receptors, can also be used to contrast vomit, nausea, giddiness, especially in case of patients subjected to chemotherapy, in the treatment of neuropathies, hemicrania, stress, diseases having a psychosomatic origin, epilepsy, Tourette syndrome, Parkinson disease, Huntington disease, Alzheimer disease, senile dementia, in case of cognitive disease and memory loss, in the treatment of problems connected to appetite (obesity, bulimia), in the treatment of pathologies of the gastrointestinal tract and of the bladder, of cardiovascular diseases, in case of urinary and fertility problems, in the treatment of neuroinflammatory pathologies as for example multiple sclerosis, Guillain-Barré syndrome, viral encephalitis.

Among the compounds object of the present invention, comprising the various isomers and respective mixtures and the corresponding hydrates or solvates and pharmaceutically acceptable salts and their pharmaceutical compositions, those having affinity towards the CB1 receptors at least five times, preferably at least ten times higher than that for the CB2 receptors, are preferably used for the treatment of diseases wherein the CB1 receptors are involved.

The compounds of formula (I) comprising the isomers and the corresponding mixtures, the corresponding hydrates or solvates or pharmaceutically acceptable salts, or in the form of the corresponding pharmaceutical compositions, having an affinity towards the CB2 receptors at least five times, preferably at least ten times higher than that for the CB1 receptors, are instead preferably used for the treatment of diseases wherein the CB2 receptors are involved.

The use of the compounds of formula (I) comprising the various isomers and their mixtures, and the corresponding hydrates or solvates and pharmaceutically acceptable salts, and the respective pharmaceutical compositions, for the treatment of the different pathologies wherein the modulation of the CB1 and/or CB2 receptors is involved as above, can be made by utilizing the known methods used for said treatments.

In particular the administration of the compounds must be carried out in a sufficiently effective amount for the specific treatment. Analogously the dosages, the administration route and the posology will be established depending on the disease typology, on the pathology seriousness, on the physical conditions, and characteristics of the patient (for example age, weight, response to the active principle), on the pharmacokinetics and toxicology of the compounds of formula (I) selected for the specific treatment.

The preferred daily dosage interval is 0.01-100 mg of compound of formula (I) of the invention per Kg of body weight of mammalian to be treated. In men, the preferred daily dosage interval is 0.1-1000 mg of compound per Kg of body weight, still more preferred from 1 to 200 mg.

A further object of the present invention is the use of compounds of formula (I), comprising the isomers and the corresponding mixtures, or of the corresponding hydrates or solvates or pharmaceutically acceptable salts, radiomarked, and of the respective pharmaceutical formulations, for the identification and marking of the cannabinoidergic CB1 or CB2 receptors in mammalians or in men.

Furthermore the compounds of formula (I) containing a hydroxyl group, comprising the isomers and the corresponding mixtures, or the corresponding hydrates or solvates or pharmaceutically acceptable salts, and the respective pharmaceutical formulations, can be used to obtain ligands, possibly detectable by immunochemical methods, to be used in the isolation, purification and characterization of the CB1 or CB2 receptors and in the identification of the corresponding active sites.

The following Examples are given to better understand the present invention and are not anyway limitative thereof.

EXAMPLES

Example 1.1

Preparation of the ethyl ester of the 5-(5-Chloro-thiophen-2-yl)-1-(2',4'-dichloro-phenyl)-4-methyl-1H-pyrazol-3-carboxylic acid

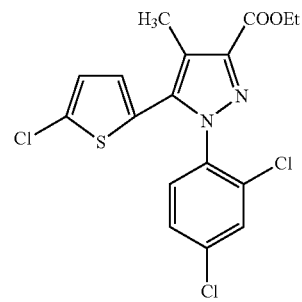

1.1a) Preparation of ethyl 4-(5-chloro-thiophen-2-yl)-3-methyl-2,4-dioxy-butyrate To a solution of 5-chloro-2-propionyl-thiophene (5.72 mmol, 1 eq) in dimethylformamide (10 ml) sodium hydride is added in dispersion in mineral oil at 60% by weight (6.87 mmoles, 1.2 eq) at a temperature of about 10° C. It is left under stirring at the indicated temperature for further 10 minutes. Lastly diethyloxalate (6.87 mmol, 1.2 eq) is added. The reaction mixture is stirred at room temperature for 3 hours, then poured in $H_2O$/ice and acidified with HCl 1N. The aqueous solution is recovered and extracted with AcOEt. The organic phase is washed with water, then dried on $Na_2SO_4$ and the solvent removed by evaporation under reduced pressure. The obtained raw product is purified by flash chromatography (oil ether/ethyl acetate 8/2 v/v on silica gel). The diketoester is isolated under the form of a yellow oil (1.37, yield 28.18%) in admixture with the starting product. Analytical characteristics of the diketoester: Rf 0.392 (oil ether/ethyl acetate 8/2 on silica gel plates); m.p. 25-26° C.; IR (nujol) ($\lambda=cm^{-1}$) 1653 (C=O); 1731 (C=O); 1751 (C=O); $^1$H-NMR (CDCl$_3$) δ 1.31 (t, 3H, J=7.0 Hz); 1.48 (d, 3H, J=7.2 Hz); 4.29 (q, 2H, J=7.0 Hz); 4.79 (q, 1H, J=7.2 Hz); 7.02 (d, 1H, J=4.2 Hz); 7.60 (d, 1H, J=4.2 Hz); Anal. calc. for $C_{11}H_{11}ClO_4S$: C, 48.09; H, 4.04; Cl, 12.90. Found: C, 48.23; H, 4.13; Cl, 12.98.

1.1b) Synthesis of the ethyl ester of the 5-(5-Chloro-thiophen-2-yl)-1-(2',4'-dichloro-phenyl)-4-methyl-1H-pyrazol-3-carboxylic acid A mixture formed of the compound obtained in the previous reaction (3.64 mmol, 1 eq) and 2,4-dichlorophenyl-hydrazine hydrochloride (4.00 mmol, 1.1 eq) in acetic acid (2 ml), was reacted at the reflux temperature for 1.5 hours. Then the mixture was cooled at room temperature, poured in water and the pH neutralized by adding a NaHCO$_3$ solution. The aqueous phase is then extracted with ethyl ether, the ether phase washed with a saturated NaHCO$_3$ solution, dried over Na$_2$SO$_4$ and concentrated by removing the solvent. A raw product was obtained which is purified by flash chromatography (oil ether/ethyl acetate 8/2 v/v) lastly isolating the ester in the form of a red-orange oil which tends to solidify (0.83 g, yield 54.97%). Rf 0.537 (oil ether/ethyl acetate 8/2, silica gel plates); m.p.: 91-92° C.; IR (nujol) ($\lambda=cm^{-1}$) 1710 (C=O); $^1$H-NMR (CDCl$_3$) δ 1.42 (t, 3H, J=7.0 Hz); 2.42 (s, 3H); 4.44 (q, 2H, J=7.0 Hz); 6.67 (d, 1H, J=4.0 Hz); 6.82 (d, 1H, J=4.0 Hz); 7.34-7.36 (m, 2H); 7.46-7.47 (m, 1H); Anal. calc. for $C_{17}H_{13}Cl_3N_2O_2S$: C, 49.12; H, 3.15; Cl, 25.58; N, 6.74. Found: C, 49.54; H, 3.18; Cl, 25.76; N, 6.88.

Example 1.2

Preparation of the ethyl ester of the 5-(5-Chloro-thiophen-2-yl)-1-(2',4'-dichloro-phenyl)-4-ethyl-1H-pyrazol-3-carboxylic acid 1.2a) Ethyl 4-(5-chloro-thiophen-2-yl)-3-ethyl-2,4-dioxy-butyrate To a solution of 5-chloro-2-butyryl-thiophene (5.72 mmol, 1 eq) in dimethylformamide (10 ml) sodium hydride was added in dispersion with mineral oil at 60% (6.87 mmoles, 1.2 eq) at a temperature of about 10° C. It is left under stirring at this temperature for further 10 min. Lastly diethyloxalate (6.87 mmoles, 1.2 eq) is added and it is reacted, under stirring, at room temperature for 3 hours. At the end the reaction mixture is poured in $H_2O$/ice and acidified with HCl 1N. The aqueous solution is then extracted with AcOEt, the organic phase recovered, washed with $H_2O$, dried over $Na_2SO_4$ and the solvent evaporated under reduced pressure. A raw product is obtained which is purified by flash chromatography (oil ether/ethyl acetate 8/2) to give a mixture of a yellow oil diketoester (0.26 g, yield 15.8%) together with the starting product. Analytical characteristics of the diketoester: Rf 0.459 (oil ether/ethyl acetate 8/2); m.p. 28-29° C.; IR (nujol) ($\lambda=cm^{-1}$) 1652 (C=O); 1730 (C=O); 1773 (C=O); $^1$H-NMR (CDCl$_3$) δ 0.99 (t, 3H, J=7.6 Hz); 1.31 (t, 3H, J=7.0 Hz); 1.91-2.16 (m, 2H); 4.28 (q, 2H, J=7.2 Hz); 4.70 (t, 1H, J=6.8 Hz); 7.02 (d, 1H, J=4.2 Hz); 7.61 (d, 1H, J=4.2 Hz); Anal. calc. for $C_{12}H_{14}ClO_4S$: C, 50.03; H, 4.55; Cl, 12.24. Found: C, 49.91; H, 4.54; Cl, 12.28.

1.2b) Preparation of the ethyl ester of the 5-(5-Chloro-thiophen-2-yl)-1-(2',4'-dichloro-phenyl)-4-ethyl-1H-pyrazol-3-carboxylic acid A mixture formed of the compound isolated in the previous step (1.73 mmoles, 1 eq) and 2,4-dichlorophenyl-hydrazine hydrochloride (1.90 mmol, 1.1 eq) in acetic acid (2 ml), was reacted at the reflux temperature for 1.5 hours and then cooled at room temperature. The reaction mixture was poured in $H_2O$, neutralized with NaHCO$_3$, then extracted with ethyl ether. The ether phase was washed with a saturated NaHCO$_3$ solution, dried over Na$_2$SO$_4$, and the solvent removed under reduced pressure. A raw product is obtained from which by flash chromatography (oil ether/ethyl acetate 8/2) the ester is isolated in the form of a white-orange solid (0.50 g, yield 67.23%). Rf 0.609 (oil ether/etyl acetate 8/2); m.p.: 91-92° C.; IR (nujol) ($\lambda=cm^{-1}$) 1712 (C=O); $^1$H-NMR (CDCl$_3$) δ 1.23 (t, 3H, J=7.6 Hz); 1.42 (t, 3H, J=7.0 Hz); 2.84 (q, 2H, J=7.4 Hz); 4.45 (q, 2H, J=7.4 Hz); 6.57 (d, 1H, J=3.6 Hz); 6.81 (d, 1H, J=3.8 Hz); 7.34-7.36 (m, 2H); 7.46-7.47 (m, 1H); Anal. calc. for $C_{18}H_{15}Cl_3N_2O_2S$: C, 50.37; H, 3.53; Cl, 24.68; N, 6.50. Found: C, 50.31; H, 3.52; Cl, 24.75; N, 6.52.

Example 1.3

Preparation of the ethyl ester of the 1-(5-Chloropen-tyl)-5-(5'-chloro-thiophen-2'-yl)-4-methyl-1H-pyra-zol-3-carboxylic acid The same method reported in the Example 1.2b was used to react the diketoester prepared in the Example 1.1a with chloropentyl hydrazine to form the pyrazol-ester compound. The purification by flash chromatography (oil ether/ethyl acetate 8/2), has given (yield 15%) an orange-coloured oil. Rf=0.23 (oil ether/ethyl acetate 8/2); m.p.: 63-64° C./2.7 mm Hg; IR (nujol) ($\lambda=cm^{-1}$) 1716 (COOEt); $^1$H-NMR (CDCl3) δ 1.34-1.44 (m, 5H); 1.66-1.88 (m, 4H); 2.23 (s, 3H); 3.48 (t, 2H, J=6.4 Hz); 4.15 (t, 2H, J=7.4 Hz); 4.42 (q, 2H, J=7.2 Hz); 6.85 (d, 1H, J=3.8 Hz); 7.00 (d, 1H, J=3.8 Hz); Anal. calc. for $C_{16}H_{20}Cl_2N_2O_2S$: C, 51.20; H, 5.37; Cl, 18.89; N, 7.46; S, 8.54. Found: C, 51.12; H, 5.37; Cl, 18.92; N, 7.49; S, 8.55.

Example 2.1

Preparation of the 5-(5-Chloro-thiophen-2-yl)-1-(2',4'-dichloro-phenyl)-4-methyl-1H-pyrazol-3-carboxylic acid To a solution in methanol (9 ml) of the ester (2 mmol, 1 eq) obtained in the Example 1.1, a methanol solution (7 ml) of KOH (4 mmol, 2 eq) was added. It is left under stirring under reflux for 8 hours. The reaction mixture is then poured in water and ice and acidified with HCl 1N. The precipitate which forms is filtered under vacuum. The solid is then washed with $H_2O$ and dried in a stove obtaining 0.67 g (yield 86.45%) of the expected acid as an analytically pure white solid. Rf 0.472 (chloroform/methanol 9/1); m.p.: 215-216°

C.; IR (nujol) ($\lambda$=cm$^{-1}$) 1686 (C=O); $^1$H-NMR (CDCl$_3$) $\delta$ 2.44 (s, 3H); 6.69 (d, 1H, J=3.6 Hz); 6.83 (s, 1H, J=3.6 Hz); 7.34-7.40 (m, 3H, OH exchanges with D$_2$O); 7.44-7.50 (m, 1H); Anal. calc. for C$_{15}$H$_9$Cl$_3$N$_2$O$_2$S: C, 46.47; H, 2.34; Cl, 27.44; N, 7.23. Found: C, 46.54; H, 2.19; Cl, 27.28; N, 7.06.

Example 2.2

Preparation of the 1-(5-Chloropentyl)-5-(5'-chloro-thiophen-2'-yl)-4-methyl-1H-pyrazol-3-carboxylic acid To a solution of the tricyclic ester prepared in the Example 1.2c (2.00 mmol, 1 eq) in methanol (10 ml), KOH (4 mmol, 2 eq) solubilized in methanol (7 ml) was added. The reaction mixture was stirred under reflux for 8 hours. Then it was poured in water and ice and acidified with HCl 1N. The solution was extracted with ethyl ether. The organic phase was anhydrified over Na$_2$SO$_4$ and then the solvent was removed under reduced pressure. The expected acid was thus obtained (yield 90%) as orange-coloured oil. Rf=0.47 (chloroform/methanolo 9/1); b.p.: 94-95° C./2.7 mm Hg; IR 1693 (C=O); $^1$H-NMR (CDCl$_3$) $\delta$ 1.37-1.48 (m, 2H); 1.64-1.88 (m, 4H); 2.26 (s, 3H); 3.50 (t, 2H, J=6.6 Hz); 4.15 (t, 2H, J=7.2 Hz); 6.87 (d, 1H, J=4.0 Hz); 7.01 (d, 1H, J=4.0 Hz); Anal. calc. for C$_{14}$H$_{16}$Cl$_2$N$_2$O$_2$S: C, 48.42; H, 4.64; Cl, 20.42; N, 8.07; S, 9.23. Found: C, 48.31; H, 4.63; Cl, 20.45; N, 8.09; S, 8.25.

ESEMPIO 2.3

Preparation of the 5-(5-Chloro-thiophen-2-yl)-1-(2',4'-dichloro-phenyl)-4-ethyl-1H-pyrazol-3-carboxylic acid To a solution in methanol (5.5 ml) of the ester prepared in the Example 1.2 (1.16 mmol, 1 eq), a KOH solution (2.23 mmol, 2 eq) in methanol (4 ml) was added. The reaction mixture was maintained under reflux under stirring overnight. At the end it is poured in water and ice and acidified with HCl 1N. The precipitate is filtered under vacuum, washed with H$_2$O and dried in a stove obtaining 0.40 g (yield 85.84%) of the acid in the form of an analytically pure white solid. Rf 0.428 (chloroform/methanol 9/1); m.p.: 207-208° C.; IR (nujol) ($\lambda$=cm$^{-1}$) 1692 (C=O); 3434 (OH); $^1$H-NMR (CDCl$_3$) $\delta$ $^1$H-NMR (CDCl$_3$): 1.25 (t, 3H, J=7.4 Hz); 2.85 (q, 2H, J=7.4 Hz); 4.81 (br s, 1H, OH exchanges with D$_2$O); 6.67 (d, 1H, J=4.0 Hz); 6.82 (d, 1H, J=4.0 Hz); 7.31-7.40 (m, 2H); 7.49 (s, 1H); Anal. calc. for C$_{16}$H$_{11}$Cl$_3$N$_2$O$_2$S: C, 47.93; H, 2.77; Cl, 26.41; N, 6.99. Found: C, 47.84; H, 2.76; Cl, 26.48; N, 6.97.

Example 3.1a

Preparation of the ester-amide adduct of the 5-(5-Chloro-thiophen-2-yl)-1-(2',4'-dichloro-phenyl)-4-methyl-1H-pyrazol-3-carboxylic acid To a suspension of the acid obtained in the Example 2.1 (0.64 mmol, 1 eq) in dichloromethane (1.3 ml), HOBt (1-hydroxybenzotriazole, 0.77 mmol, 1.2 eq) and EDC (1-(3-diamino propyl)-3-ethylcarbodiimide hydrochloride, 0.77 mmol, 1.2 eq) were added. The solution was maintained under stirring at room temperature for 30 min, then used as such to prepare the compounds described hereinafter in the Examples 3.1b-3.1g, without isolating the amide which was formed.

Example 3.1b

Preparation of N-piperidinyl-5-(5-Chloro-thiophen-2-yl)-1-(2',4'-dichloro-phenyl)-4-methyl-1H-pyrazol-3-carboxamide The solution containing the ester-amide adduct prepared in the Example 3.1a was added, by quick dripping, to a solution of 1-aminopiperidine (1.28 mmol, 2 eq) in dichloromethane (2 ml). The reaction mixture was stirred at room temperature for 30 min.

After having removed the solvent, the obtained product was treated with oil ether and purified by flash chromatography (oil ether/ethyl acetate 8/2) obtaining 0.16 g (yield 55.17%) of carboxamide in the form of a white solid. Rf 0.25 (oil ether/ethyl acetate 8/2); m.p.: 125-126° C.; IR (nujol) ($\lambda$=cm$^{-1}$) 1662 (C=O); 3213 (NH); $^1$H-NMR (CDCl$_3$) $\delta$ 1.38-1.50 (m, 2H); 1.69-1.80 (m, 4H); 2.45 (s, 3H); 2.85 (t, 4H, J=5.6 Hz); 6.65 (d, 1H, J=4.0 Hz); 6.81 (d, 1H, J=4.0 Hz); 7.30-7.36 (m, 2H, NH exchanges with D$_2$O); 7.49-7.51 (m, 1H); 7.61 (s, 1H); $^{13}$C-NMR (CDCl$_3$) $\delta$ 9.56 (CH$_3$); 23.33 (CH$_2$); 25.40 (2×CH$_2$); 57.08 (2×CH$_2$); 119.44 (C); 126.39 (CH); 127.79 (C); 127.97 (CH); 128.17 (CH); 130.22 (C); 130.32 (CH); 130.75 (CH); 130.84 (C); 133.73 (C); 135.62 (C); 136.54 (C); 144.28 (C) 159.70 (CO); Anal. calc. for C$_{20}$H$_{19}$Cl$_3$N$_4$OS: C, 51.13; H, 4.08; Cl, 22.64; N, 11.93. Found: C, 51.24; H, 4.09; Cl, 22.58; N, 11.90.

Example 3.1c

Preparation of N-homopiperidinyl-5-(5-Chloro-thiophen-2-yl)-1-(2',4'-dichloro-phenyl)-4-methyl-1H-pyrazol-3-carboxamide The solution containing the ester-amide adduct prepared in the Example 3.1a was added, by quick dripping, to a solution of 1-amino-homo-piperidine (1.28 mmol, 2 eq) in dichloromethane (2 ml). The reaction mixture was stirred at room temperature for 30 min. After having removed the solvent, the obtained product was treated with oil ether and purified by flash chromatography (oil ether/ethyl acetate 8/2) obtaining 0.10 g (yield 32.26%) of carboxamide in the form of a white solid. Rf 0.375 (oil ether/ethyl acetate 8/2); m.p.: 134-135° C.; IR (nujol) ($\lambda$=cm$^{-1}$) 1660 (C=O); 3289 (NH); $^1$H-NMR (CDCl$_3$) $\delta$ 1.60-1.80 (m, 8H); 2.46 (s, 3H); 3.14 (t, 4H, J=5.8 Hz); 6.65 (d, 1H, J=4.0 Hz); 6.81 (d, 1H, J=4.0 Hz); 7.32-7.35 (m, 2H); 7.49-7.51 (m, 1H); 8.02 (br s, 1H, NH exchanges with D$_2$O); $^{13}$C-NMR (CDCl$_3$) $\delta$ 9.56 (CH$_3$); 26.30 (2×CH$_2$); 26.94 (2×CH$_2$); 58.33 (2×CH$_2$); 119.31 (C); 126.37 (CH); 127.32 (C); 127.94 (CH); 128.13 (CH); 130.29 (CH); 130.72 (CH); 132.41 (C); 132.71 (C); 135.62 (C); 136.48 (C); 136.89 (C) 144.23 (C) 160.02 (CO); Anal. calc. for C$_{21}$H$_{21}$Cl$_3$N$_4$OS: C, 52.13; H, 4.37; Cl, 21.98; N, 11.58. Found: C, 52.04; H, 4.35; Cl, 22.02; N, 11.61.

Example 3.1d

Preparation of N-pyrrolidinyl-5-(5-Chloro-thiophen-2-yl)-1-(2',4'-dichloro-phenyl)-4-methyl-1H-pyrazol-3-carboxamide The solution containing the ester-amide adduct prepared in the Example 3.1a was added, by quick dripping, to a solution of 1-aminopyrrolidine hydrochloride (1.28 mmol, 2 eq) and TEA (1.28 mmol, 2 eq) in dichloromethane (2 ml). The reaction mixture was stirred at room temperature for 30 min. After having removed the solvent, the obtained product was treated with oil ether and purified by flash chromatography (oil ether/ethyl acetate 7/3) obtaining 0.37 g (yield 77.42%) of carboxamide as a white solid. Rf 0.178 (oil ether/ethyl acetate 7/3); m.p.: 187-188° C.; IR (nujol) ($\lambda$=cm$^{-1}$) 1664 (C=O); 3215 (NH); $^1$H-NMR (CDCl$_3$) $\delta$ 1.82-1.95 (m, 4H); 2.46 (s, 3H); 2.94-3.05 (m, 4H); 6.65 (d, 1H, J=3.8 Hz); 6.81 (d, 1H, J=3.8 Hz); 7.33-7.36 (m, 2H); 7.49-7.51 (m, 1H); 7.58 (br s, 1H, NH exchanges with D$_2$O); $^{13}$C-NMR (CDCl$_3$) $\delta$ 9.57 (CH$_3$); 22.21 (2×CH$_2$); 54.41 (2×CH$_2$); 119.32 (C); 126.38 (CH); 127.27 (C); 127.96 (CH); 128.15 (CH); 130.31 (CH); 130.72 (CH); 132.44 (C); 133.73 (C); 135.59 (C); 136.54 (C); 136.96 (C) 144.22 (C) 160.57 (CO); Anal. calc. for C$_{19}$H$_{17}$Cl$_3$N$_4$OS: C, 50.07; H, 3.76; Cl, 23.03; N, 12.29. Found: C, 50.12; H, 3.77; Cl, 23.27; N, 12.31.

Example 3.1e

Preparation of N-phenyl-5-(5-Chloro-thiophen-2-yl)-1-(2',4'-dichloro-phenyl)-4-methyl-1H-pyrazol-3-carboxamide The solution containing the ester-amide adduct prepared in the Example 3.1a was added, by quick dripping, to an aniline solution (1.28 mmol, 2 eq) in dichloromethane (2 ml). The reaction mixture was stirred at room temperature for 1 h. After having removed the solvent, the obtained product was treated with oil ether and purified by flash chromatography (oil ether/ethyl acetate 8/2) obtaining 0.33 g (yield 56.67%) of carboxamide in the form of a solid. Rf 0.661 (oil ether/ethyl acetate 8/2); m.p. 175-176° C.; IR (nujol) ($\lambda$=cm$^{-1}$) 1676 (C=O); 3378 (NH); $^1$H-NMR (CDCl$_3$) $\delta$ 2.52 (s, 3H); 6.69 (d, 1H, J=3.8 Hz); 6.83 (d, 1H, J=3.8 Hz); 7.11 (t, 1H, J=7.4 Hz); 7.31-7.43 (m, 4H); 7.53 (s, 1H); 7.67 (d, 2H, J=7.8 Hz); 8.74 (br s, 1H, NH exchanges with D$_2$O); $^{13}$C-NMR (CDCl$_3$) $\delta$ 9.72 (CH$_3$); 119.45 (C); 119.72 (CH x2); 124.07 (CH); 126.44 (CH); 127.10 (C); 128.01 (CH); 128.36 (CH); 128.97 (CH×2); 130.36 (CH); 130.69 (CH); 132.63 (C); 133.76 (C); 135.53 (C); 136.67 (C); 137.48 (C); 137.76 (C); 144.74 (C); 160.24 (CO); Anal. calc. for C$_{21}$H$_{14}$Cl$_3$N$_3$OS: C, 54.50; H, 3.05; Cl, 22.98; N, 9.08; S, 6.93. Found: C, 54.36; H, 2.98; Cl, 22.79; N, 8.95; S, 6.87.

Example 3.1f

Preparation of N-phenyl-5-(5-Chloro-thiophen-2-yl)-1-(2',4'-dichloro-phenyl)-4-methyl-1H-pyrazol-3-carbohydrazide

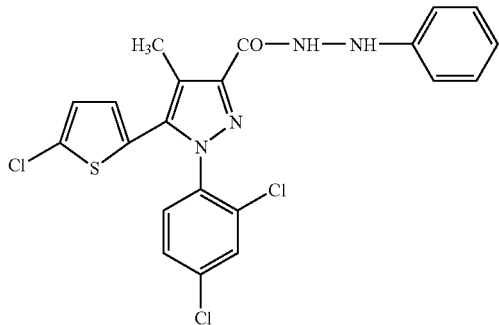

The solution containing the ester-amide adduct prepared in the Example 3.1a was added, by quick dripping, to a solution of phenylhydrazine hydrochloride (1.28 mmol, 2 eq) and TEA (1.28 mmol, 2 eq) in dichloromethane (2 ml). The reaction mixture was stirred at room temperature for 30 min. After having removed the solvent, the obtained product was treated with oil ether and purified by flash chromatography (oil ether/ethyl acetate 8/2) obtaining 0.38 g (yield 62.10%) of the expected product as a yellow solid. Rf 0.321 (oil ether/ethyl acetate 8/2); m.p.: 154-155° C.; IR (nujol) ($\lambda$=cm$^{-1}$) 3302 (NH); 3187 (NH); 1680 (CO); $^1$H-NMR (CDCl$_3$) $\delta$ 2.44 (s, 3H); 6.18 (d, 1H, NH exchanges with D$_2$O); 6.68 (d, 1H, J=3.8 Hz); 6.83 (d, 1H, J=3.8 Hz); 6.90-6.98 (m, 3H); 7.20-7.30 (m, 2H); 7.37-7.38 (m, 2H); 7.53 (s, 1H); 8.56 (d, 1H, NH exchanges with D$_2$O); $^{13}$C-NMR (CDCl$_3$) $\delta$ 9.49 (CH$_3$); 113.61 (CH×2); 119.54 (C); 121.20 (CH); 126.46 (CH); 127.30 (C); 128.03 (CH); 128.32 (CH); 129.17 (CH x2); 130.39 (CH); 130.63 (CH); 132.67 (C); 133.66 (C); 135.51 (C); 136.68 (C); 137.18 (C); 143.16 (C); 148.16 (C); 162.39 (CO); Anal. calc. for C$_{21}$H$_{15}$Cl$_3$N$_4$OS: C, 52.79; H, 3.16; Cl, 22.26; N, 11.73. Found: C, 52.71; H, 3.16; Cl, 22.23; N, 11.75.

Example 3.1g

Preparation of the ester-amide adduct of the 1-(5-Chloro pentyl)-5-(5'-chloro-thiophen-2'-yl)-4-methyl-1H-pyrazol-3-carboxylic acid To a suspension of the acid obtained in the Example 2.2 (0.64 mmol, 1 eq) in dichloromethane (1.3 ml), HOBt (1-hydroxybenzothiazole 0.77 mmol, 1.2 eq) and EDC (0.77 mmol, 1.2 eq) were added. The solution was stirred at room temperature for 30 min, then used as such for preparing the compound described in the Example 3.1h.

Example 3.1h

Preparation of N-Piperidinyl-1-(5-chloropentyl)-5-(5'-chloro-thiophen-2'-yl)-4-methyl-1H-pyrazol-3-carboxamide The solution of the compound prepared in the Example 3.1 g was added, by quick dripping, to a solution of 1-aminopiperidine (1.28 mmol, 2 eq) in dichloromethane (2 ml). The reaction mixture was stirred at room temperature for 30 min. After having removed the solvent, the obtained product was purified by flash chromatography (oil ether/ethyl acetate 8/2) obtaining a yellow oil which was treated with oil ether to obtain the expected product as a white solid (23% yield). Rf 0.16 (oil ether/ethyl acetate 7/3); m.p.: 72-73° C.; IR (nujol) ($\lambda$=cm-1) 1662 (C=O); 3217 (NH); $^1$H-NMR (CDCl3) $\delta$ 1.37-1.56 (m, 4H); 1.71-1.82 (m, 8H); 2.27 (s, 3H); 2.88 (t, 4H, J=5.8 Hz); 3.51 (t, 2H, J=6.4 Hz); 4.06 (t, 2H, J=7.2 Hz); 6.81 (d, 1H, J=3.8 Hz); 6.98 (d, 1H, J=3.6 Hz); 7.59 (s, 1H, NH exchanges with D$_2$O); $^{13}$C-NMR (CDCl$_3$) $\delta$ 9.26 (CH$_3$); 23.39 (CH$_2$); 23.78 (CH$_2$); 25.47 (2×CH$_2$); 29.56 (CH$_2$); 31.85 (CH$_2$); 44.63 (CH$_2$); 49.78 (CH$_2$); 57.11 (2×CH$_2$); 120.11 (C); 126.70 (CH); 127.78 (C); 129.02 (CH); 132.56 (C); 134.63 (C); 141.83 (C) 160.15 (CO); Anal. calc. for C$_{19}$H$_{26}$Cl$_2$N$_4$OS: C, 53.14; H, 6.10; Cl, 16.51; N, 13.05; S, 7.47. Found: C, 52.98; H, 6.08; Cl, 16.55; N, 13.08; S, 7.48.

Examples of other compounds of formula (I) are described in Table 1. The starting acids used are those of the Examples and 2.2; the syntheses were carried out analogously to what described in the Examples 3.1a-3.1h., by using reactants known in the prior art.

TABLE I (I)

[Structure: 1-(2,4-dichlorophenyl)-5-(5-chlorothien-2-yl)-4-B-pyrazole-3-carboxamide with CO—NH—T' group]

| Ex. | B | T¹ | Yield (%) | m.p. (°C.) | Empirical Formula | IR (λ = cm⁻¹) | ¹H-NMR (δ ppm) |
|---|---|---|---|---|---|---|---|
| 3.1i | $CH_3$ | (2,6,6-trimethyl-bicycloheptyl-ethyl group) | 78.26 | 58-62 | $C_{25}H_{26}Cl_3N_3OS$ | 3423 (NH), 1676 (C = O); | 0.82-0.94 (m, 2H); 1.07 (s, 3H); 1.19 (s, 3H); 1.45-1.62 (m, 1H); 1.82-2.04 (m, 4H); 2.21-2.43 (m, 2H); 2.47 (s, 3H); 3.26-3.57 (m, 2H); 6.65 (d, 1H, J = 3.6 Hz); 6.81 (d, 1H, J = 3.4 Hz); 6.94 (t, 1H); 7.31-7.39 (m, 2H); 7.51 (s, 1H); |
| 3.1l | $CH_2CH_3$ | N-methylpiperidinyl | 57.85 | 152-153 | $C_{21}H_{21}Cl_3N_4OS$ | 3162 (NH), 1650 (C = O); | 1.25 (t, 3H, J = 7.2 Hz); 1.35-1.51 (m, 2H); 1.65-1.83 (m, 4H); 2.77-2.97 (m, 6H); 6.64 (d, 1H, J = 3.8 Hz); 6.80 (d, 1H, J = 3.8 Hz); 7.32-7.39 (m, 2H); 7.50 (s, 1H); 7.62 (brs, 1H, NH exchanges with $D_2O$); |
| 3.1m | $CH_2CH_3$ | N-azepanyl | 56.22 | 84-85 | $C_{22}H_{23}Cl_3N_4OS$ | 3167 (NH), 1653 (C = O); | 1.25 (t, 3H, J = 7.4 Hz); 1.54-1.83 (m, 8H); 2.87(q, 2H, J = 7.6Hz); 3.14 (t, 4H, J = 4.8 Hz); 6.63 (d, 1H, J = 4.0 Hz); 6.80 (d, 1H, J = 3.6Hz); 7.31-7.39 (m, 2H); 7.49 (s, 1H); 8.02 (br s, 1H, NH exch. with $D_2O$); |
| 3.1n | $CH_2CH_3$ | N-pyrrolidinyl | 63.83 | 134-135 | $C_{20}H_{19}Cl_3N_4OS$ | 3233 (NH), 1667 (C = O) | 1.25 (t, 3H, J = 7.6 Hz); 1.86-1.93 (m, 4H); 2.88 (q, 2H, J = 7.2 Hz); 2.95-3.05 (m, 4H); 6.64 (d, 1H, J = 4.0 Hz); 6.80 (d, 1H, J = 4.0 Hz); 7.33-7.35 (m, 2H); 7.49 (s, 1H); 7.59 (br s, 1H, NH exchanges with $D_2O$); |
| 3.1o | $CH_2CH_3$ | phenyl | 54.62 | 194-195 | $C_{22}H_{16}Cl_3N_3OS$ | 3381 (NH), 1675 (C = O); | 1.29 (t, 3H, J = 7.4 Hz); 2.94 (q, 2H J = 7.6 Hz); 6.68 (d, 1H, J = 3.8 Hz); 6.83 (d, 1H, J = 4.0 Hz); 7.11 (t, 1H, J = 7.6 Hz); 7.31-7.38 (m, 4H); 7.52 (s, 1H); 7.68 (d, 2H, J = 8.8 Hz); 8.77 (br s, 1H, NH exchanges with $D_2O$); |
| 3.1p | $CH_2CH_3$ | —NH—phenyl | 60.98 | 58-62 | $C_{22}H_{17}Cl_3N_4OS$ | 3416 (NH), 3283 (NH), 1681 (C = O); | 1.22 (t, 3H, J = 7.4 Hz); 2.85 (q, 2H J = 7.2 Hz); 6.20 (br s, 1H, NH exch. with $D_2O$); 6.66 (d, 1H, J = 4.0 Hz); 6.82 (d, 1H, J = 4.0 Hz); 6.90-6.97 (m, 3H); 7.20-7.28 (m, 2H); 7.36-7.37 (m, 2H); 7.52 (s, 1H); 8.56 (br s, 1H, NH exchanges with $D_2O$); |
| 3.1q | $CH_3$ | —$(CH_2)_4$—$CH_3$ | 24 | 887-88 | $C_{20}H_{20}Cl_3N_3OS$ | 3420 (NH), 1721 (C = O); | 0.82-0.95 (m, 3H); 1.26-1.39 (m, 4H); 1.51-1.63 (m, 2H); 2.47 (s, 3H); 3.40 (q, 2H, J = 6.6 Hz); 6.66 (d, 1H, J = 4.0 Hz); 6.81 (d, 1H, J = 3.6 Hz); 6.93 (br s, 1H, exchanges with $D_2O$); 7.32-7.37 (m, 2H); 7.48-7.53 (m, 1H); |

TABLE I-continued

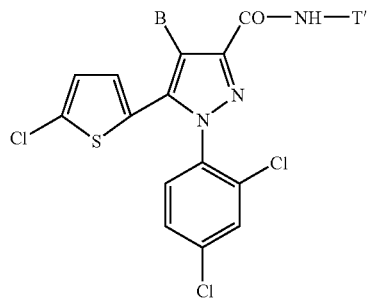

(I)

| Ex. | B | T¹ | Yield (%) | m.p. (° C.) | Empirical Formula | IR (λ = cm⁻¹) | ¹H-NMR (δ ppm) |
|---|---|---|---|---|---|---|---|
| 3.1r | CH$_2$CH$_3$ |  | 78.36 | 52-54 | C$_{26}$H$_{28}$Cl$_3$N$_3$OS | 3424 (NH), 1681 (C = O); | 0.87 (s, 1H); 0.92 (s, 1H); 1.07 (s, 3H); 1.19 (s, 3H); 1.25 (t, 3H); 1.51-1.62 (m, 1H); 1.82-2.02 (m, 4H); 2.22-2.40 (m, 2H); 2.89 (q, 2H); 3.31-3.54 (m, 2H); 6.64 (d, 1H, J = 3.8 Hz); 6.80 (d, 1H, J = 3.4 Hz); 6.95 (t, 1H, NH exchanges with D$_2$O); 7.32-7.35 (m, 2H); 7.51 (s, 1H) |

Example 4

Affinity Towards the Cannabinoidergic CB1 and CB2 Receptors

The affinity of the compounds of the present invention towards the cannabinoidergic CB1 and CB2 receptors was evaluated in vitro through radioreceptorial binding studies by utilizing the method reported below.

The receptorial binding technique allows indeed to establish if and with what affinity and specificity a determined compound binds itself to a particular receptor. To evaluate the affinity of a determined compound towards a particular receptor, a particular preparation of the tissue wherein the receptors are present is used and the tested compound is made to compete with another compound, treated so as to make it radioactive and of which the affinity for the receptor is known. The capability of the tested compound to remove the radioactive compound gives an index of the affinity by which the compound binds itself to that determined receptor. The reading of the radioactivity present in the receptor-compound complex allows furthermore to precisely calculate the compound amount bound to the receptor. By this method it is therefore possible to rapidly identify the affinity of a new compound towards a specific receptor and thus to make predictions on its pharmacological activity. By repeating the same experimental scheme it is possible to evaluate the affinity of the compound towards other kinds of receptors and thus establish the specificity degree.

The receptorial binding technique, besides being used for the screening of new molecules having a pharmacological activity, can give useful information on possible changes at a receptorial level correlated for example to a prolonged exposure to drugs and/or to particular pathologies. As a matter of fact, in these situations, changes in the amount of the receptors present or structural changes can be pointed out which alter the agonist or antagonist affinity and consequently influence the normal function of the receptors themselves.

The experimentation was carried out according to the guide lines of the European Community for the animal experimentation (EEC No. 86/609), by employing laboratory animals (rats) housed in groups of twenty for cage, under standard stalling conditions (temperature 22±2° C., relative humidity 60%, artificial lighting with a 12 hour light-dark cycle). Food and water were available ad libitum.

The procedure used, based on the employment of the compound [³H]-CP-55,940 (New England Nuclear, Boston, Mass., USA), implies the utilization of rat brain as biological tissue for the evaluation of the affinity towards the CB1 receptors and of rat spleen for the affinity determination towards the CB2 receptors.

The animals were sacrificed by cervical dislocation, the brain in toto (cerebellum excluded) and the spleen were rapidely dissected and maintained in ice.

The tissue was homogenized in 15 volumes (weight/volume) of TME buffer (50 mM Tris, 1 mM EDTA e 3 mM MgCl$_2$, pH 7.4) by an Ultra-Turrax and centrifuged for 10 minutes at 1086×g in a centrifuge cooled at 4° C. The resulting supernatant was centrifuged at 45,000×g for 30 min at 4° C. by using a Beckman SW41 rotor and the final pellet was resuspended in 50 volumes of TME.

The obtained membranes (50-80 μg of proteins) were incubated in the presence of 1 nM di [³H]-CP55,940 for 1 h at 30° C. in a final volume of 0.5 ml of TME buffer containing 5 mg/ml of bovine serum albumin (BSA). The non specific binding was measured in the presence of CP55,940 at the 1 μM concentration. All the experiments were carried out in polypropylene test tubes pretreated with Sigma-Cote (Sigma Chemical Co. Ltd., Poole, UK) to reduce the non specific binding.

For the building of the competitive inhibition binding curves eight different concentrations of each compound were used. As reference compounds SR141716A for the CB1 receptors and SR144528 for the CB2 receptors were utilized.

Incubation was interrupted by addition of TME buffer (at 4° C.) containing 5 mg/ml of BSA and filtration under vacuum through Whatman GFC filters pretreated with 0.5% of polyethyllamine (PEI) and by using a filtering apparatus (Brandell, Gaithersburg, Md., USA). Filters were washed 3 times with 5 ml of Tris HCl buffer (pH 7.4, 4° C.) containing 1 mg/ml of BSA and singly placed in plastic vials containing 4 ml of liquid for scintigraphy (Ultima Gold MV, Packard).

The radioactivity present in the filters was measured by a scintillator spectrophotometer (Tricarb 2100, Packard, Meridien, USA).

The protein determination was carried out by the Bradford method by using the protocol and the reactants supplied by Bio-Rad (Milano, Italia).

The experiments were carried out in triplicate and the results confirmed in five independent experiments.

The affinity of the compounds towards the CB1 and CB2 receptors was expressed in Ki terms.

Table 4 shows the Ki values obtained with the compounds of the present invention, examined in the test in vitro. The affinity of the compounds of the present invention is compared with that relating to the reference compounds SR144528 and SR141716A (Rimonobant®).

The Table shows that the compounds of the present invention have activity on the CB1 and/or CB2 receptors comparable with that of the prior art compounds active on said receptors.

Example 5

Hypothermia Tests In Vivo

As said, the compounds having cannabimimetic activity show in vivo the following effects: hypoactivity, hypothermia, analgesia and catalepsy (B. R. Martin et al., *Pharmacol. Biochem. Behav.;* 1991, 40, 471-478; P. B. Smith et al.; *J. Pharmacol. Exp. Ther.;* 1994, 270, 219-227). To be able to exert the thermoregulation function, the compounds having activity towards the cannabinoidergic receptors must be capable to pass the hemato-encephalic barrier, the central site of said receptors regulating the temperature being positioned in the preoptical front nucleus of the hypothalamus (S. M. Rawls et al.; *J. Pharmacol. Exp. Ther.;* 2002, 303, 395-402). Following treatments with CB1 agonist compounds capable to pass the hemato-encephalic barrier, the cannabimimetic activity pointed out itself by the registration of a reduction of the body temperature. In the case of CB1 antagonist compounds capable to pass the hemato-encephalic barrier, the treatment with said compounds does not imply any body temperature variation, however it implies an antagonist activity towards reference CB1 agonists as WIN 55,212-2, thus contrasting the hypothermia induced by the latter.

To evaluate the activity in vivo of the compounds of general formula (I), tests were therefore carried out to evaluate the hypothermia induced as a result of treatments carried out with said compounds. Tests were carried out in the experiment animal (rat) according to the work indications by M. Rinaldi-Carmona et al. in *FEBS Letters;* 1994, 350, 240-244. The rectal temperature in the rat was determined by an electronic thermometer inserted at a 2 mm depth. The measurements were carried out on rats acclimated for one hour. The rectal temperature was determined before and after (from 30 to 120 minutes) the i.p. administration of the compound to be tested.

When no temperature reduction following the administration of the compound to be tested was pointed out, it was evaluated the antagonist activity of the same towards a reference CB1 agonist compound as WIN 55,212-2. For this purpose the rectal temperature measurements were carried out upon i.p. administration of the compound to be tested 30 minutes before the WIN 55,212-2 administration. The compounds capable to pass the hemato-encephalic barrier and to antagonise the CB1 agonist activity of WIN 55,212-2 are indeed capable to contrast the temperature reduction induced by the reference agonist.

Each test was repeated on ten animals; the reported results are the average of the results obtained with the ten animals.

The Examples reported hereinafter show that the invention compounds (I) (Examples 5.1 and 5.2), having affinity towards the CB1 receptors as it has been shown in the tests in vitro of the Examples 4, are able to pass the hemato-encephalic barrier. In particular the compounds of formula (I) of the Examples 5.1 and 5.2, not having as such any effect on the body temperature, but being able to contrast the temperature reduction induced by WIN 55,212-2, are CB1 antagonists.

Example 5.1

The test was carried out with the compound of the Example 3.1c. Aqueous samples were used wherein the compound of the Example 3.1c was dispersed in water with three drops of Tween 80. Following the above procedure, treatments were carried out with doses (mg compound/kg of body weight) respectively of 0.1; 0.5; 1.0; 3.0; 6.0.

In none of the examined cases there was a reduction of the body temperature in the treated rats with respect to the physiological solution administration (38° C.).

In the case of the evaluation of the antagonist activity towards WIN 55,212-2 (3 mg compound/kg of body weight), substantial variations of the body temperature were instead pointed out with respect to the treatment with the only WIN 55,212-2. In particular the compound of the Example 3.1b was able to antagonize the effect of WIN 55,212-2 (CB1 agonist), contrasting the effect of the reduction of the body temperature induced by the CB1 agonist administration.

The compound of the Example 3.1b is thus capable to pass the hemato-encephalic barrier and shows a CB1 antagonist behaviour.

The temperatures detected during the experiment, from the zero time (i.p. administration of the CB1 agonist WIN 55,212-2)) up to 120 min are reported in Table 5.

Example 5.2

The Example 5.1 was repeated but with the compound of the Example 3.1d instead of that of the Example 3.1b.

As in case of the compound of the Example 3.1b, also the compound of the Example 3.1d does not cause as such any effect on the body temperature. Said compound is able to pass the hemato-encephalic barrier antagonizing the effect of the CB1 agonist WIN 55,212-2.

With none of the doses employed a reduction of the body temperature in the treated rats was indeed noticed. In the case of the evaluation of the antagonist activity towards WIN 55,212-2 (3 mg compound/kg of body weight), substantial variations of the body temperature were instead pointed out with respect to the treatment with the only WIN 55,212-2. In particular the compound of the Example 3.1d was able to antagonize the effect of WIN 55,212-2 (CB1 agonist), contrasting the effect of the reduction of the body temperature induced by the CB1 agonist administration.

The temperatures detected during the experiment, from zero time (i.p. administration of the CB1 agonist WIN 55,212-2) up to 120 min are reported in Table 6.

Example 6

Intestinal Motility Tests

To further evaluate the activity in vivo of the compounds (I) object of the present invention, functional tests were carried out to evaluate the effect of said compounds on the rat intestinal motility. It was indeed shown the involvement of the cannabinoidergic CB1 receptors in the intestinal motility regulation in rat (R. G. Pertwee et al; *Br. J. Pharmacol.*; 1996, 118, 2199-2205). In particular, the CB1 receptor agonists slacken the gastrointestinal motility; antagonist compounds of the same receptors have instead a prokinetic effect on the gastrointestinal transit (G. Colombo et al.; *Eur. J. Pharmacol.*; 1998, 344, 67-69; M. A. Casu et al.; *Eur. J. Pharmacol.*; 2003, 459, 97-105).

The evaluation of the constipating or prokinetic effect of the compounds was carried out by the Upper Gut Transit Test method on the basis of the procedure defined and ratified by Y. Nagakura et al.; *Eur. J. Pharmacol.*; 1996, 311, 67-72. The method, which allows to measure the motility of the stomach and of the first intestine tract (small or little intestine), implies:

the administration of the compound to be tested by i.p. route;

the administration of carmine red (marker not directly absorbable from the stomach) by intragastric route through a metal probe, after 20 minutes from the administration of the compound to be tested;

the rat sacrifice by cervical dislocation after a prefixed time (30 minutes) starting from the administration time;

the intestine explant from pylorus to the ileo-cecal valve;

the determination of the intestinal part crossed by the marker;

the data processing to determine the percentage of crossed part with respect to the total length of the small intestine.

With respect to the control (physiological solution or carrier wherein the compounds to be tested were solubilized or dispersed), the administration of CB1 agonist compounds implies a reduction of the intestinal transit percentage; an opposite effect is noticed in case of antagonist compounds. The latter are therefore capable to cancel the constipating effect of CB1 agonist compounds.

Each test was repeated on ten animals; the results reported in the Examples are the average of the results obtained with ten animals.

The Examples reported hereinafter show that the invention compounds (I) are active on the gastrointestinal tract. In particular the compounds of the Examples 3.1b and 3.1d increase the intestinal transit rate and are capable to antagonize the effect of a CB1 agonist as the compound WIN 55,212-2, implying a prokinetic effect on the gastrointestinal tract.

Example 6.1

The test was carried out with the compound of the Example 3.1b; aqueous samples were in particular used wherein the compound 3.1b was dispersed in water with three drops of Tween 80. According to the above procedure, with treatments respectively equal to 0.5 and 1.0 mg of compound/kg of body weight, the marker has run on an average an intestinal portion equal to, respectively, 1.57 and 1.76 times the length run from the marker in the intestine following the administration of a physiological solution containing the same amount of Tween 80.

The prokinetic effect of the compound of the Example 3.1b was evaluated also towards the constipating action of the CB1 agonist compound WIN 55,212-2. The treatment of rats with aqueous samples of WIN 55,212-2 with concentrations equal to 0.5 mg of compound/kg of body weight, has implied a covering of the intestinal transit from the marker equal to 0.16 times the length run from the marker in the intestine following the administration of a physiological solution containing the same above indicated amount of Tween 80. In the case of similar treatment with WIN 55,212-2 preceded by the administration of an aqueous sample of the compound of the Example 3.1b with concentration equal to 1.0 mg of compound/kg of body weight, the marker has instead run, on an average, the same length run in the intestine following the administration of a physiological solution containing the same amount of Tween 80. The compound of the Example 3.1b, under the above conditions, was therefore capable to antagonize the constipating effect of the CB1 agonist WIN 55,212-2.

Example 6.2

The Example 6.1 was repeated but by using the compound of formula (I) of the Example 3.1d at the place of the compound of the Example 3.1b. With treatments respectively equal to 0.5 and 1.0 mg of compound/kg of body weight, the marker has run on an average an intestinal portion respectively equal to 1.61 and to 1.74 times the length run by the marker in the intestine following the administration of a physiological solution containing the same amount of Tween 80.

In this case also the prokinetic effect of the compound of the Example 3.1d was evaluated towards the constipating action of the CB1 agonist compound WIN 55,212-2. The rat treatment with aqueous samples of WIN 55,212-2 with concentrations equal to 0.5 mg of compound/kg of body weight, has implied a covering of the intestinal transit from the marker equal to 0.16 times the length covered by the marker in the intestine following the administration of a physiological solution containing the same above indicated amount of Tween 80. In case of similar treatment with WIN 55,212-2 preceded by the administration of an aqueous sample of the compound of the Example 3.1d with concentration equal to 0.5 mg of compound/kg of body weight, the marker has instead run on an average the same length run in the intestine following the administration of a physiological solution containing the same amount of Tween 80. The compound of the Example 3.1d was thus able, under the above conditions, to antagonize the constipating effect of the CB1 agonist WIN 55,212-2.

TABLE 4

Example 4: activity in vitro of the invention compounds on the CB1 and CB2 receptors, compared with that of the reference compounds SR144528 and SR141716A

| Compound (Ex.) | CB1 (brain) $K_i$ (nM) | CB2 (spleen) $K_i$ (nM) |
|---|---|---|
| 3.1b | 35.0 ± 2.5 | 476.0 ± 3.0 |
| 3.1c | 21.0 ± 1.0 | 270.0 ± 5.0 |
| 3.1d | 63.0 ± 7.2 | 699.0 ± 21.0 |
| SR144528 (comp) | 70 ± 10 | 0.28 ± 0.04 |
| SR141716A(comp) | 1.8 ± 0.075 | 514 ± 30 |

TABLE 5

Pharmacological Example 5.1: trend of the body temperature after administration in rat (10 animals) of WIN 55,212-2 as such or in combination with the compound of the Example 3.1b in the doses indicated in the Table. The average animal body temperature after administration of a physiological solution is 38° C.

| Time from the administration of WIN 55,212-2 (minutes) | WIN 55,212-2 (3 mg/kg) | WIN 55,212-2 (3 mg/kg) + compound Ex. 3.1b (conc in mg/kg) | | | | |
|---|---|---|---|---|---|---|
| | | 0.1 | 0.5 | 1.0 | 3.0 | 6.0 |
| 0 | 37.9 | 38.5 | 38.1 | 38.3 | 38.4 | 38.6 |
| 15 | 35.6 | 35.1 | 35.8 | 36.1 | 36.1 | 37.7 |
| 30 | 33.8 | 33.8 | 34.5 | 35.7 | 35.7 | 37.9 |
| 60 | 34.5 | 35.3 | 35.7 | 36.8 | 36.8 | 37.9 |
| 90 | 35.8 | 36.9 | 36.7 | 37.8 | 37.8 | 38.2 |
| 120 | 36.8 | 37.3 | 37.3 | 37.9 | 37.9 | 37.9 |

TABLE 6

Pharmacological Example 5.2: trend of the body temperature after administration in rat (10 animals) of WIN 55,212-2 as such or in combination with the compound of the Example 3.1d in the doses indicated in the Table. The body temperature after administration of a physiological solution is 38° C.

| Time from the administration of WIN 55,212-2 (minutes) | WIN 55,212-2 (3 mg/kg) | WIN 55,212-2 (3 mg/kg) + compund Ex. 3.1d (conc. in mg/kg) | | | | |
|---|---|---|---|---|---|---|
| | | 0.1 | 0.5 | 1.0 | 3.0 | 6.0 |
| 0 | 37.9 | 38.1 | 38.1 | 37.9 | 38.4 | 37.8 |
| 15 | 35.6 | 35.3 | 35.7 | 36.5 | 37.0 | 36.9 |
| 30 | 33.8 | 33.8 | 34.4 | 34.7 | 36.8 | 36.9 |
| 60 | 34.5 | 35.6 | 35.0 | 35.8 | 37.3 | 37.2 |
| 90 | 35.8 | 36.5 | 36.3 | 36.7 | 37.7 | 37.8 |
| 120 | 36.8 | 37.2 | 37.2 | 37.1 | 37.6 | 37.9 |

The invention claimed is:

1. A Pyrazole derivative of formula (I), having affinity for the cannabinoidergic CB1 and/or CB2 receptors:

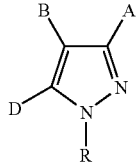

(I)

R is aryl, not substituted or having from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle, and phenyl;

A is an amidic substituent of formula —C(O)—NH—T', wherein T' is a group $NR_1R_2$, wherein $R_1$ and $R_2$ are equal or different and have the following meanings:

$C_1$-$C_7$ alkyl;

aryl, arylalkyl or arylalkenyl not substituted or optionally having on the aromatic rings from one to four substituents, equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy, wherein in the previous substituents comprising $C_1$-$C_7$ aliphatic chains, $C_1$-$C_3$ chains are preferably used; wherein $R_1$ may additionally be hydrogen;

or $R_1$ and $R_2$ together with the nitrogen atom to which they are linked form a, saturated or unsaturated, heterocycle from 5 to 10 atoms comprising carbon atoms and including the nitrogen of $NR_1R_2$, and optionally an additional S, O or N atom, not substituted or optionally having from one to four substituents, equal to or different from each other, selected from $C_1$-$C_7$ alkyl, phenyl, and benzyl, said phenyl or benzyl optionally substituted with one or more groups, equal to or different from each other, selected from: halogen, $C_1$-$C_7$ alkyl, $C_1$-$C_7$ haloalkyl, $C_1$-$C_7$ haloalkoxy, $C_1$-$C_7$ alkylthio and $C_1$-$C_7$ alkoxy;

B is a group selected from: hydrogen and $C_1$-$C_4$ alkyl; and

D is an heteroaryl with a ring size of from 5 to 6 atoms, selected from the group consisting of thiophene, pyridine, furan, oxazole, thiazole, imidazole, pyrazole, isoxazole, isothiazole, triazole, pyridazine, pyrimidine, pyrazine, triazine and pyrrole; wherein the heteroaryl is optionally substituted with one, two, three or four substituents, equal to or different from each other, selected from the following: halogen, $C_1$-$C_3$ alkyl, $C_1$-$C_3$ alkylthio, $C_1$-$C_3$ alkoxy, $C_1$-$C_3$ haloalkyl, and $C_1$-$C_3$ haloalkoxy.

2. A compound according to claim 1, wherein:

R is aryl containing from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle and phenyl;

B is a $C_1$-$C_4$ alkyl.

3. A compound according to claim 1, wherein:

R is aryl, not substituted or having from one to five substituents, equal to or different from each other, selected from halogen, $C_1$-$C_3$ alkyl, $C_1$-$C_3$ alkylthio, $C_1$-$C_3$ alkoxy, $C_1$-$C_3$ haloalkyl, and $C_1$-$C_3$ haloalkoxy;

B is a $C_1$-$C_3$ alkyl;

D is an heteroaryl selected from the following: thiophene, pyridine, furan, oxazole, thiazole, imidazole, pyrazole, isoxazole, isothiazole, triazole, pyridazine, pyrimidine, pyrazine, triazine, and pyrrole; said heteroaryls optionally substituted with one, two, three or four substituents, equal to or different from each other, selected from the following: halogen, $C_1$-$C_3$ alkyl, $C_1$-$C_3$ alkylthio, $C_1$-$C_3$ alkoxy, $C_1$-$C_3$ haloalkyl, and $C_1$-$C_3$ haloalkoxy.

4. A compound according to claim 1, wherein A=—C(O)—NH—T', wherein T' is a group $NR_1R_2$ wherein $R_1$ is not hydrogen.

5. A compound according to claim 4, selected from the following:

N-piperidinyl-5-(5-chloro-thiophen-2-yl)-1-(2',4'-dichlorophenyl)-4-methyl-1H-pyrazole-3-carboxamide;

N-homopiperidinyl-5-(5-chloro-thiophen-2-yl)-1-2',4'-dichlorophenyl)-4-methyl-1H-pyrazol-3-carboxamide;

N-pyrrolidinyl-5-(5-chloro-thiophen-2-yl)-1-(2',4'-dichlorophenyl)-4-methyl-1H-pyrazol-3-carboxamide;

p-Methoxyphenyl-5-(5-chloro-thiophen-2-yl)-1-(2',4'-dichlorophenyl)-4-methyl-1H-pyrazol-3-carbohydrazide;
N-piperidinyl-5-(5-bromo-thiophen-2-yl)-1-(2',4'-dichlorophenyl)-4-methyl-1H-pyrazol-3-carboxamide;
N-homopiperidinyl-5-(5-bromo-thiophen-2-yl)-1-(2',4'-dichlorophenyl)-4-methyl-1H-pyrazol-3-carboxamide;
N-pyrrolidinyl-5-(5-bromo-thiophen-2-yl)-1-(2',4'-dichlorophenyl)-4-methyl-1H-pyrazol-3-carboxamide;
p-Methoxyphenyl-5-(5-bromo-thiophen-2-yl)-1-(2',4'-dichlorophenyl)-4-methyl-1H-pyrazol-3-carbohydrazide;
N-piperidinyl-5-(5-methyl-thiophen-2-yl)-1-(2',4'-dichlorophenyl)-4-methyl-1H-pyrazol-3-carboxamide;
N-homopiperidinyl-5-(5-methyl-thiophen-2-yl)-1-(2',4'-dichlorophenyl)-4-methyl-1H-pyrazol-3-carboxamide;
N-pyrrolidinyl-5-(5-methyl-thiophen-2-yl)-1-(2',4'-dichlorophenyl)-4-methyl-1H-pyrazol-3-carboxamide;
p-Methoxyphenyl-5-(5-methyl-thiophen-2-yl)-1-(2',4'-dichlorophenyl)-4-methyl-1H-pyrazol-3-carbohydrazide;
N-piperidinyl-5-(5-chloro-thiophen-2-yl)-1-(2',4'-dichlorophenyl)-4-ethyl-1H-pyrazol-3-carboxamide;
N-homopiperidinyl-5-(5-chloro-thiophen-2-yl)-1-(2',4'-dichlorophenyl)-4-ethyl-1H-pyrazol-3-carboxamide;
N-pyrrolidinyl-5-(5-chloro-thiophen-2-yl)-1-(2',4'-dichlorophenyl)-4-ethyl-1H-pyrazol-3-carboxamide;
p-Methoxyphenyl-5-(5-chloro-thiophen-2-yl)-1-(2',4'-dichlorophenyl)-4-ethyl-1H-pyrazol-3-carbohydrazide;
N-piperidinyl-5-(5-bromo-thiophen-2-yl)-1-(2',4'-dichlorophenyl)-4-ethyl-1H-pyrazol-3-carboxamide;
N-homopiperidinyl-5-(5-bromo-thiophen-2-yl)-1-(2',4'-dichlorophenyl)-4-ethyl-1H-pyrazol-3-carboxamide;
N-pyrrolidinyl-5-(5-bromo-thiophen-2-yl)-1-(2',4'-dichlorophenyl)-4-ethyl-1H-pyrazol-3-carboxamide;
p-Methoxyphenyl-5-(5-bromo-thiophen-2-yl)-1-(2',4'-dichlorophenyl)-4-ethyl-1H-pyrazol-3-carbohydrazide;
N-piperidinyl-5-(5-methyl-thiophen-2-yl)-1-(2',4'-dichlorophenyl)-4-ethyl-1H-pyrazol-3-carboxamide;
N-homopiperidinyl-5-(5-methyl-thiophen-2-yl)-1-(2',4'-dichlorophenyl)-4-ethyl-1H-pyrazol-3-carboxamide;
N-pyrrolidinyl-5-(5-methyl-thiophen-2-yl)-1-(2',4'-dichlorophenyl-4-ethyl-1H-pyrazol-3-carboxamide; and
p-Methoxyphenyl-5-(5-methyl-thiophen-2-yl)-1-(2',4'-dichlorophenyl)-4-ethyl-1H-pyrazol-3-carbohydrazide.

6. A compound according to claim 1 wherein the compound comprises chiral cores.

7. A compound according to claim 1 wherein the compound is a cis isomer or a trans isomer.

8. A pharmaceutically acceptable salt of the compound:

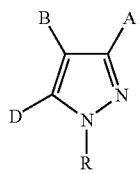

(I)

wherein R is aryl, not substituted or having from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle and phenyl;

A is an amidic substituent of formula —C(O)—NH—T', wherein T' is a group $NR_1R_2$, wherein $R_1$ and $R_2$ are equal or different and have the following meanings:

$C_1$-$C_7$ alkyl;

aryl, arlylalkyl or arylalkenyl not substituted or optionally having on the aromatic rings from one to four substituents, equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy, wherein in the previous substituents comprising $C_1$-$C_7$ aliphatic chains, $C_1$-$C_3$ chains are preferably used;

wherein $R_1$ may additionally be hydrogen;

or $R_1$, and $R_2$ together with the nitrogen atom to which they are linked form a, saturated or unsaturated, heterocycle from 5 to 10 atoms, comprising carbon atoms and including the nitrogen of $NR_1R_2$, and optionally an additional S, O or N atom not substituted or optionally having from one to four substituents, equal to or different from each other, selected from $C_1$-$C_7$ alkyl, phenyl, and benzyl, said phenyl or benzyl optionally substituted with one or more groups, equal to or different from each other, selected from: halogen, $C_1$-$C_7$ alkyl, $C_1$-$C_7$ haloalkyl, $C_1$-$C_7$ haloalkoxy, $C_1$-$C_7$ alkylthio and $C_1$-$C_7$ alkoxy;

B is a group selected from: hydrogen and $C_1$-$C_4$ alkyl; and

D is an heteroaryl with a ring size of from 5 to 6 atoms, selected from the group consisting of thiophene, pyridine, furan, oxazole, thiazole, imidazole, pyrazole, isoxazole, isothiazole, triazole, pyridazine, pyrimidine, pyrazine, triazine and pyrrole; wherein the heteroaryl is optionally substituted with one, two, three or four substituents, equal to or different from each other, selected from the following: halogen, $C_1$-$C_3$ alkyl, $C_1$-$C_3$ alkylthio, $C_1$-$C_3$ alkoxy, $C_1$-$C_3$ haloalkyl, and $C_1$-$C_3$ haloalkoxy.

9. A pharmaceutical comprising a compound of formula (I) according to claim 1.

10. A pharmaceutical according to claim 9 comprising sodium alkylsulphate or another surfactant.

11. A pharmaceutical composition comprising 0.5-20% by weight of a compound according to claims 1-8, 0.05-0.5% by weight of sodium alkylsulphate or another surfactant, 2.5-10% by weight of a disgregating agent.

* * * * *

UNITED STATES PATENT AND TRADEMARK OFFICE
CERTIFICATE OF CORRECTION

PATENT NO. : 7,659,407 B2
APPLICATION NO. : 11/134627
DATED : February 9, 2010
INVENTOR(S) : Lazzari et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this

Thirtieth Day of November, 2010

David J. Kappos
*Director of the United States Patent and Trademark Office*